(12) United States Patent
Gilardi et al.

(10) Patent No.: US 6,927,039 B2
(45) Date of Patent: Aug. 9, 2005

(54) ENZYMATIC PROCESS

(75) Inventors: Gianfranco Gilardi, London (GB); Anthony Edward George Cass, London (GB); Georgia Eleni Tsotsou, Reutlingen (DE)

(73) Assignee: Nanobiodesign Limited, London (GB)

( * ) Notice: Subject to any disclaimer, the term of this patent is extended or adjusted under 35 U.S.C. 154(b) by 348 days.

(21) Appl. No.: 10/182,554

(22) PCT Filed: Jan. 30, 2001

(86) PCT No.: PCT/GB01/00373

§ 371 (c)(1),
(2), (4) Date: Nov. 25, 2002

(87) PCT Pub. No.: WO01/57236

PCT Pub. Date: Aug. 9, 2001

(65) Prior Publication Data

US 2003/0186347 A1 Oct. 2, 2003

(30) Foreign Application Priority Data

Jan. 31, 2000 (GB) .............................. 0002201

(51) Int. Cl.[7] .............................. C12Q 1/26; C12Q 1/00
(52) U.S. Cl. ............................................ 435/25; 435/4
(58) Field of Search ...................................... 435/25, 4

(56) References Cited

U.S. PATENT DOCUMENTS

| | | | |
|---|---|---|---|
| 4,303,752 A | * 12/1981 | Kolehmainen et al. | 435/8 |
| 4,542,098 A | 9/1985 | Vandecasteele et al. | 435/190 |
| 4,954,445 A | 9/1990 | Yoshihama et al. | 435/191 |
| 5,780,239 A | * 7/1998 | Carter et al. | 435/7.1 |
| 6,060,253 A | 5/2000 | Krausz et al. | 424/130.1 |

FOREIGN PATENT DOCUMENTS

| | | |
|---|---|---|
| JP | 4 258289 A | 9/1992 |
| WO | WO 99 60096 A | 11/1999 |
| WO | WO 00 31273 A | 6/2000 |
| WO | WO 01 11086 A | 2/2001 |

OTHER PUBLICATIONS

Schwaneberg et al., "A continuous spectrophotometric assay for P450 BM–3, a fatty acid hydroxylating enzyme, and its mutant F87A," *Analytical Biochemistry*, Academic Press, vol. 269, No. 2 (May 1999), pp. 359–366.

Peterson et al., "P450BM–3: A tale of two domains—or is it three?" *Steroids: Structure, Function, and Regulation*, US, Elsevier Science Publishers, vol. 62, No. 1 (1997), pp. 117–123.

Schwaneberg et al, "P450 monooxygenase in biotechnology—1. Single–step, large–scale purification method for cytochrome P450 BM–3 by anion–exchange chromatography," *Journal of Chromatography*, NL, Elsevier Science Publishers B.V Amsterdam, vol. 848, No. 1–2 (July 1999), pp. 149–159.

* cited by examiner

*Primary Examiner*—Louise N. Leary
(74) *Attorney, Agent, or Firm*—Sughrue Mion, PLLC

(57) ABSTRACT

A process is described for detecting modulation of NAD (P)H and/or a NAD(P)H dependent oxidoreductase ("NDO") in or by a biological system which comprises NAD(P)H and an NDO. The process comprises generating a detectable marker of NAD(P)H modulation, and detecting said detectable marker.

11 Claims, 9 Drawing Sheets

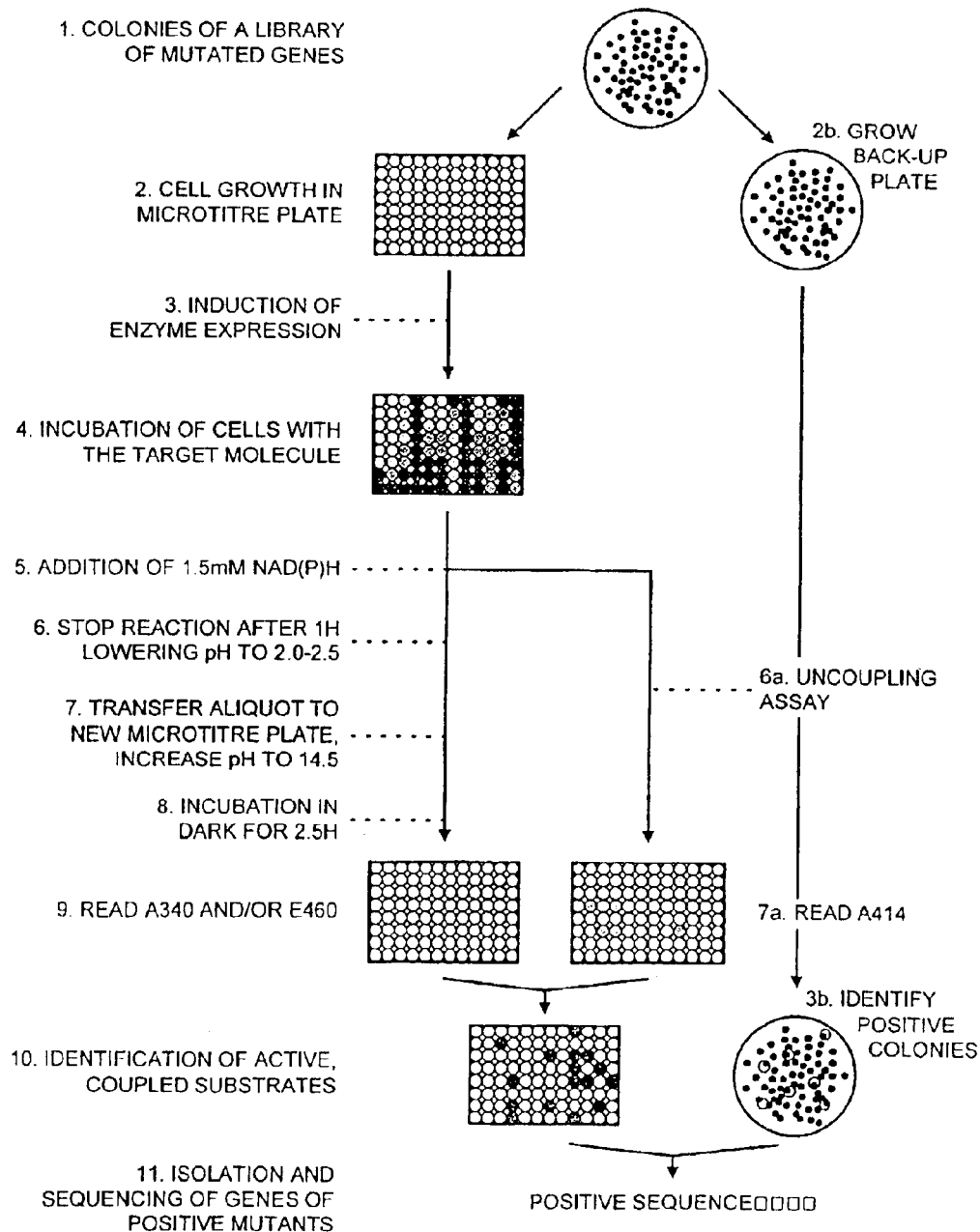

ENZYMATIC PROCESS

FIELD OF INVENTION

Figure 1:
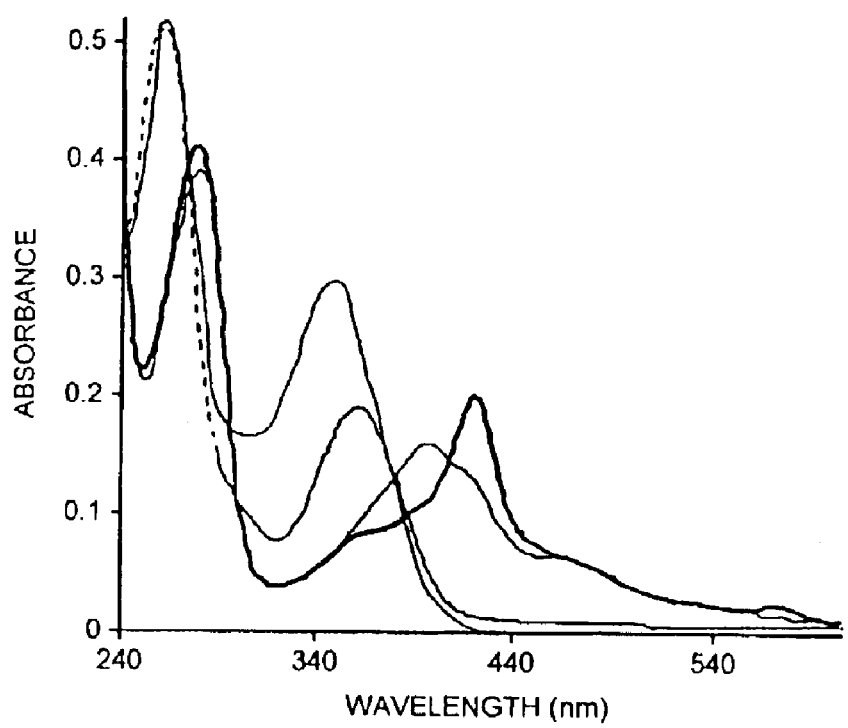
Figure 1:
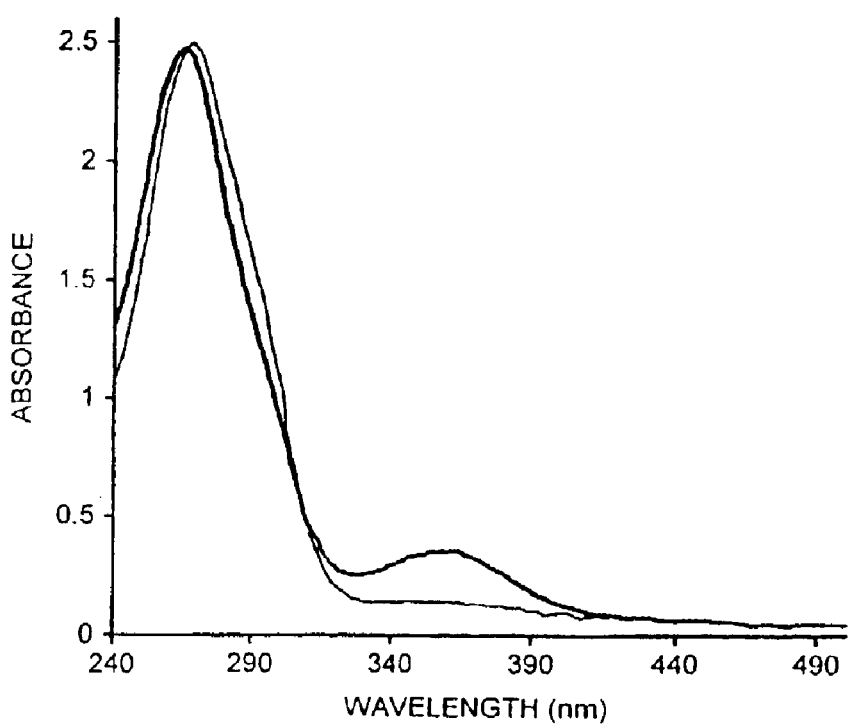

The present invention relates to a process. In particular, the present invention relates to an assay method.

More in particular, the present invention relates to an assay method for identifying whether a candidate agent can modulate NAD(P)H and/or a NAD(P)H dependent oxidoreductase ("NDO") and/or for determining whether NAD(P)H and/or an NDO can modulate an entity and/or for identifying or detecting one or more key catalytic activities associated with the modulation of NAD(P)H and/or an NDO.

BACKGROUND ART

The use of combinatorial methods in both chemistry and biochemistry over the last few years has generated an enormous number of (bio)molecules of pharmaceutical (drugs) and biotechnological (biocatalysts) interest. The ability to effectively identify active molecules in random libraries relies on the availability of a screening method able to select the positive variants or derivatives that can be further characterised and commercialised. An ideal, general screening method would be able to select the positive targets from a random library of molecules/substrates tested against a specific binding protein/enzyme, as well as to select positive, active variants of a random library of binding proteins/enzymes against a specific target molecule/substrate.

It is desirable to identify agents that can modulate NAD(P)H and/or an NDO. This is because NAD(P)H is a ubiquitous cofactor required by many oxidoreductases of biotechnological interest. NAD(P)H-dependent oxidoreductases are widely spread in nature, carrying out a great number of reactions that can be of biotechnological interest. The availability of a screening method that would allow for workers to identify potential substrates for these heterogeneous class of enzymes, or for the activity of a library of random mutants with different specificities towards selected targets, would be of great importance for engineering purposes. In particular, cytochromes P450 are widespread enzymes in nature involved both in biosynthetic and biodegradation pathways. The wide range of their functions and specificity presents attractive possibilities for their use in different applications, such as large scale chemical synthesis and drug metabolite production, toxicity screening tests of drugs or chemicals as well as detoxification of waste and in situ bioremediation of contaminated areas (1).

The present invention seeks to provide an effective assay method for identifying agents that could modulate NAD(P)H and/or an NDO (or even vice versa).

SUMMARY ASPECTS OF THE PRESENT INVENTION

In a broad aspect, the present invention relates to a process for detecting modulation of NAD(P)H in or by a biological system; said process comprising generating a detectable marker of NAD(P)H, and detecting said detectable marker.

The present invention is based on finding that it is possible to have an assay method for detecting the modulation of NAD(P)H and/or a NAD(P)H dependent oxidoreductase ("NDO"). The modulation can occur in or by a biological system. Typically the biological system comprises NAD(P)H and an NDO. The assay method comprises generating a detectable marker of NAD(P)H and/or NDO modulation in said biological system, and detecting said detectable marker. As used herein, the NDO may be the protein/enzyme or in some cases it may even be a nucleotide sequence coding for same. Preferably, however, the NDO is the protein/enzyme.

The present invention is advantageous as it provides a commercially useful assay to identify suitable agents that could be used in vivo to treat conditions associated with NAD(P)H and/or an NDO.

The present invention is also advantageous as it provides a commercially useful assay to identify mutant NDO(s) that may have importance in, for example, chemical synthetic processes.

Thus, the process of the present invention provides a means for the detection of the NAD(P)H consumption or generation, preferably in whole cells expressing a NAD(P)H-dependent target enzyme. Thus, the availability of a screening method that provides for the identifaction of potential substrates for these heterogeneous class of enzymes, or for the activity of a library of random mutants with different specificities towards selected targets, is of great importance for engineering purposes.

DETAILED ASPECTS OF THE PRESENT INVENTION

In one aspect, the present invention relates to a process for detecting modulation of NAD(P)H and/or a NAD(P)H dependent oxidoreductase ("NDO") in or by a biological system which comprises NAD(P)H and an NDO; said process comprising generating a detectable marker of NAD(P)H and/or NDO modulation, and detecting said detectable marker.

In another aspect, the present invention relates to a method comprising the steps of: (a) performing the process according to the present invention; (b) identifying one or more agents that are capable of modulating NAD(P)H and/or NDO; and (c) preparing a quantity of those one or more identified agents.

In a further aspect, the present invention relates to agents identified by the process of the present invention.

In a further aspect, the present invention relates to a method of in vivo modulating NAD(P)H and/or NDO with an agent; wherein the agent is capable of modulating NAD(P)H and/or NDO by an assay method (such as an in vitro assay method); wherein the in vitro assay method is the process of the present invention.

In a further aspect, the present invention relates to the use of an agent in the preparation of a pharmaceutical composition for the treatment of a disease or condition associated with NAD(P)H and/or NDO, wherein the agent is the agent identified by the process of the present invention and/or wherein the agent is capable of modulating NAD(P)H and/or NDO when assayed (such as in vitro) by the process of the present invention.

In a further aspect, the present invention relates to a method of treating a subject with an agent, wherein the agent is the agent identified by the process of the present invention and/or wherein the agent is capable of modulating NAD(P)H and/or NDO when assayed (such as in vitro) by the process of the present invention.

In a further aspect, the present invention relates to a method of in vivo modulating an entity with NAD(P)H and/or NDO; wherein NAD(P)H and/or NDO is capable of modulating the entity by an assay method (such as an in vitro assay method); wherein the in vitro assay method is the process of the present invention.

In a further aspect, the present invention relates to a biological system for use in a process for detecting modulation of NAD(P)H and/or a NAD(P)H dependent oxidoreductase ("NDO"), wherein said biological system comprises NAD(P)H and an NDO; wherein said biological system is capable of generating a detectable marker of NAD(P)H and/or NDO modulation.

In a further aspect, the present invention relates to a biological system for use in a process for detecting modulation of NAD(P)H and/or a NAD(P)H dependent oxidoreductase ("NDO"), wherein said biological system comprises NAD(P)H and an NDO; wherein said biological system is capable of generating a detectable marker of NAD(P)H and/or NDO modulation; wherein said biological system is an *E. coli* cell; and wherein said NDO is cytochrome P450 BM3 from *Bacillus megaterium*.

In a further aspect, the present invention relates to a method comprising the steps of: (a) performing the process according to the present invention; (b) identifying one or more mutant NDO(s) that are capable of being modulated; and (c) preparing a quantity of those one or more mutant NDO(s).

In a further aspect, the present invention relates to mutant NDO(s) identified by the process of the present invention.

In a further aspect, the present invention relates to a method comprising the steps of: (a) performing the process according to the present invention; (b) identifying one or more NDO fragments, derivatives or homologues thereof that are capable of being modulated; and (c) preparing a quantity of those one or more NDO fragments, derivatives or homologues thereof.

In a further aspect, the present invention relates to NDO fragments, derivatives or homologues thereof identified by the process of the present invention.

For ease of reference, these and further aspects of the present invention are now discussed under appropriate section headings. However, the teachings under each section are not necessarily limited to each particular section.

Preferable Aspects

Preferably said biological system comprises whole cell(s).

Preferably said biological system also comprises a substrate for said NDO.

Preferably said substrate is a putative biologically useful agent.

Preferably said biologically useful agent is for use in or as a pharmaceutical and/or for use in environmentally associated industries and/or for use in synthetic processes for preparing chemicals etc. and/or for use in waste (re)cycling processes.

Preferably said detectable marker is, or is based on an analogue of, $NAD(P)^+$.

Preferably said detectable marker is generated by alkaline treatment of $NAD(P)^+$.

Preferably said NAD(P)H modulation is NAD(P)H consumption.

In the process, preferably a substance is added that mops up any unwanted/residual NAD(P)H before said alkaline treatment.

Preferably said substance is HCl.

Preferably said process further comprises the step of quantifying said modulation.

Preferably said detection is via spectrometric techniques.

Preferably, said spectrometric techniques are absorbance or emission spectrometric techniques.

Preferably said NAD(P)H consumption is linked to metabolism of one or more xenobiotic compounds.

Preferably said NAD(P)H consumption is the result of oxygenase activity.

Preferably said NDO is a mono-oxygenases.

Preferably said NDO is a cytochrome P450.

Preferably said NDO is a cytochrome P450 that is catalytically self-sufficient.

Preferably said NDO is cytochrome P450 BM3 from *Bacillus megaterium*.

For some embodiments, preferably the biological system oxygen is present.

For some embodiments, preferably the biological system is contained within a reservoir. Preferably the reservoir is a microtitre plate.

Preparation of the Biological System

The biological system may be prepared in any suitable manner. By way of example, if the biological system is a cell then the NDO may be expressed in said cell by use of recombinant DNA techniques. Then the cell comprising said NDO is placed in a reservoir to which is then added the substrate and then NAD(P)H is added. However, for some embodiments, the NAD(P)H and the substrate may be added together. For some embodiments, the cell is added to the NAD(P)H and/or the substrate which NAD(P)H and/or substrate is/are located in reservoir.

NAD(P)H

The term NAD(P)H is used in its normal sense—i.e. as meaning NADPH or NADH. The term $NAD(P)^+$ is used as meaning $NADP^+$ or $NAD^+$. As it is well known, NADP is nicotinamide-adenine dinucleotide phosphate, NAD is nicotinamide-adenine dinucleotide phosphate, NADPH is nicotinamide-adenine dinucleotide phosphate (reduced) and NADH is nicotinamide-adenine dinucleotide (reduced).

NAD(P)H Dependent Oxidoreductase

The NAD(P)H dependent oxidoreductase ("NDO") may be any suitable NDO.

By way of example, the NDO may be a wild type ("WT") enzyme, or it may be the same as a WT enzyme, or it may be a mutant, variant, fragment or derivative thereof.

If the NDO is a mutant then that mutant may be prepared from a mutated nucleotide sequence, which mutated nucleotide sequence may be prepared by standard techniques—such as one or more of: site directed mutagenesis, random mutagenesis, forced evolution, and other recombinant DNA techniques etc.

If the NDO is a variant, fragment or derivative of a WT enzyme or a mutant thereof then that then that variant, fragment or derivative may be prepared from an appropriately amended nucleotide sequence, which amended nucleotide sequence may be prepared by standard techniques—such as by use of appropriate restriction enzymes, recombinant DNA techniques etc.

The NDO may be isolated from natural sources or it may be expressed from recombinant DNA.

By way of example, the biological system may comprise the NDO or nucleotide coding for same affixed to a solid support.

The NDO may be a natural constituent of the cell and/or may be recombinantly expressed.

Preferably, the biological system is a cell. When the biological system is a cell, the NDO may be a natural constituent of the cell and/or may be recombinantly expressed.

Preferably, the NDO is recombinantly expressed in said cell. In this embodiment, the recombinantly expressed NDO may be the same as the natural NDO in the cell (i.e. the NDO is over expressed in a cell). Alternatively, the recombinantly expressed NDO may be different (such as mutant, variant, fragment or derivative form) in a cell that naturally expresses a NDO. In the latter embodiment, said natural NDO expression may be suppressed or removed or absent from said cell.

Preferably said NDO is a mono-oxygenase.

Typically the NDO is a NAD(P)H dependent oxidoreductase belonging to one of the following classes (ENZYME—The Enzyme Data Bank): class 1.1.1, class 1.2.1, class 1.3.1, class 1.4.1, class 1.5.1, class 1.6.1, class 1.7.1, class 1.8.1, class 1.9.1, class 1.10.1, class 1.11.1, class 1.12.1, class 1.16.1, class 1.17.1, class 1.18.1, class 1.14.12, class 1.14.13, class 1.14.14, class 1.14.15, class 1.14.16, class 1.14.99.

Cytochrome P450 BM3

Preferably the NDO is a cytochrome P450.

Preferably the NDO is a cytochrome P450 that is catalytically self-sufficient.

Preferably the NDO is cytochrome P450 BM3 from *Bacillus megaterium*.

Cytochrome P450 BM3 is a soluble cytoplasmic P450 enzyme, isolated from *Bacillus megaterium*. One of its unique features is that it is a catalytically self-sufficient P450 mono-oxygenase system, containing on a single polypeptide chain both a monooxygenase and a reductase domain. P450 BM3 catalyses with high efficiency and very strong coupling the mono- (and poly-)oxygenation of long-chain fatty acids or fatty acid amides and alcohols by oxygen with NADPH as external electron donor (2–6). Recently novel substrates of P450 BM3 have been identified, indicating that the range of substrates of P450 BM3 is broader than was originally believed (7–9). The combination of these characteristics with the great potential offered by new protein engineering methods able to design the properties of the active site opens a wide range of opportunities for biotechnological exploitation (10). Rational design of mutants by site-directed mutagenesis has been widely applied to P450 cam (10, 11) and P450 BM3 (12–16). A much greater potential is offered by the application of random mutagenesis methods. These have already given a range of successful examples of enzyme optimisation (improvement in enzymatic activity, substrate specificity, protein folding and expression levels) with emerging applications to pharmaceuticals and vaccines (17–19). However investigating the substrate specificity of an enzyme and expanding it to molecules of interest by random mutagenesis techniques demands an efficient screening method. Several screening methods for cytochromes P450 have been reported in the literature (20–24). Most of these screening systems were dependent on the direct or indirect detection of the product of the turnover of certain substrates by the enzyme. Although such methods may be adapted for high throughput assays, their application is limited to P450 enzymes with particular specificity screened. To date there has been reported in the literature only one case of random mutagenesis of the P450 BM3 (20). In that study a small library of random P450 BM3 mutants was created and screened by comparing carbon monoxide geminate recombination kinetics. Although this method has the advantage that it detects alterations specifically in the substrate binding pocket of the enzyme, its important drawbacks are that it is not sufficiently efficient for screening pools of mutants and that it can only be applied on cell lysates, as opposed to whole cells.

Modulation

The process of the present invention is useful for detecting agents that modulate NAD(P)H and/or an NDO. Here, the modulation can be interaction of the agent with NAD(P)H and/or with the NDO. In the latter case, the agent may be a substrate for the NDO. The modulation effect can influence the activity of the NAD(P)H and/or the activity of the NDO—such as increasing activity or decreasing activity or ensuring activity or causing activity—towards each other or towards a substrate. The modulation can be NAD(P)H consumption or generation.

Substrate

The substrate may be a natural substrate or a synthetic compound.

The substrate may even be the agent that is to be tested.

The substrate may be an organic compound or other chemical. The substrate can be an amino acid sequence or a chemical derivative thereof, or a combination thereof. The substrate may even be a nucleotide sequence—which may be a sense sequence or an anti-sense sequence. The substrate may even be an antibody.

Agent

The agent may be an organic compound or other chemical. The agent can be an amino acid sequence or a chemical derivative thereof, or a combination thereof. The agent may even be a nucleotide sequence—which may be a sense sequence or an anti-sense sequence. The agent may even be an antibody.

If the agent is an organic compound then, for some applications, that organic compound may typically comprise an —(SO$_2$)— and/or a OH group and/or an amide group and one or more hydrocarbyl groups. Here, the term "hydrocarbyl group" means a group comprising at least C and H and may optionally comprise one or more other suitable substituents. Examples of such substituents may include halo-, alkoxy-, nitro-, an alkyl group, a cyclic group etc. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain hetero atoms. Suitable hetero atoms will be apparent to those skilled in the art and include, for instance, sulphur, nitrogen and oxygen. For some applications, preferably the agent comprises at least one cyclic group. Examples of compounds are presented in the Examples section herein.

Amino Acid Sequence

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "protein".

The amino acid sequence may be prepared isolated from a suitable source, or it may be made synthetically or it may be prepared by use of recombinant DNA techniques.

In one aspect, the present invention provides an amino acid sequence that is capable of acting as a target in an assay for the identification of one or more agents and/or derivatives thereof capable of affecting the interaction of NAD(P)H and an NDO.

Nucleotide Sequence

As used herein, the term "nucleotide sequence" is synonymous with the term "polynucleotide".

The nucleotide sequence may be DNA or RNA of genomic or synthetic or of recombinant origin. The nucleotide sequence may be double-stranded or single-stranded whether representing the sense or antisense strand or combinations thereof.

For some applications, preferably, the nucleotide sequence is DNA.

For some applications, preferably, the nucleotide sequence is prepared by use of recombinant DNA techniques (e.g. recombinant DNA).

For some applications, preferably, the nucleotide sequence is cDNA.

For some applications, preferably, the nucleotide sequence may be the same as the naturally occurring form for this aspect.

In one aspect, the present invention provides a nucleotide sequence that is capable of acting as a target in an assay for the identification of one or more agents and/or derivatives thereof capable of affecting the interaction of NAD(P)H and an NDO.

Variants/Homologues/Derivatives

In addition to the specific amino acid sequences and nucleotide sequences mentioned herein, the present invention also encompasses the use of variants, homologue and derivatives thereof. Here, the term "homology" can be equated with "identity".

In the present context, an homologous sequence is taken to include an amino acid sequence which may be at least 75, 85 or 90% identical, preferably at least 95 or 98% identical. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403–410) and the GENEWORKS suite of comparison tools. Both BLAST and FASTA are available for offline and online searching (see Ausubel et al., 1999 ibid, pages 7–58 to 7–60).

However it is preferred to use the GCG Bestfit program.

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

A further useful reference is that found in FEMS Microbiol Lett 1999 May 15; 174(2):247–50 (and a published erratum appears in FEMS Microbiol Lett 1999 August 1; 177(1):187–8).

Once the software has produced an optimal alignment, it is possible to calculate % homology, preferably % sequence identity. The software typically does this as part of the sequence comparison and generates a numerical result.

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

Expression Vectors

The nucleotide sequence for use as the target or for expressing the target can be incorporated into a recombinant replicable vector. The vector may be used to replicate and express the nucleotide sequence in and/or from a compatible host cell. Expression may be controlled using control sequences which include promoters/enhancers and other expression regulation signals. Prokaryotic promoters and promoters functional in eukaryotic cells may be used. Tissue specific or stimuli specific promoters may be used. Chimeric promoters may also be used comprising sequence elements from two or more different promoters described above.

The protein produced by a host recombinant cell by expression of the nucleotide sequence may be secreted or may be contained intracellularly depending on the sequence and/or the vector used. The coding sequences can be designed with signal sequences which direct secretion of the substance coding sequences through a particular prokaryotic or eukaryotic cell membrane.

Fusion Proteins

The target amino acid sequence may be produced as a fusion protein, for example to aid in extraction and purification. Examples of fusion protein partners include glutathione-S-transferase (GST), 6xHis, GAL4 (DNA binding and/or transcriptional activation domains) and galactosidase. It may also be convenient to include a proteolytic cleavage site between the fusion protein partner and the protein sequence of interest to allow removal of fusion protein sequences. Preferably the fusion protein will not hinder the activity of the target.

The fusion protein may comprise an antigen or an antigenic determinant fused to the substance of the present invention. In this embodiment, the fusion protein may be a non-naturally occurring fusion protein comprising a substance which may act as an adjuvant in the sense of providing a generalised stimulation of the immune system. The antigen or antigenic determinant may be attached to either the amino or carboxy terminus of the substance.

In another embodiment of the invention, the amino acid sequence may be ligated to a heterologous sequence to encode a fusion protein. For example, for screening of peptide libraries for agents capable of affecting the substance activity, it may be useful to encode a chimeric substance expressing a heterologous epitope that is recognised by a commercially available antibody.

Antibody

As indicated, the agent to be tested in the assay method of the present invention may be an antibody.

The "antibody" as used herein includes but is not limited to, polyclonal, monoclonal, chimeric, single chain, Fab fragments and fragments produced by a Fab expression library. Such fragments include fragments of whole antibodies which retain their binding activity for a target substance, Fv, F(ab') and F(ab')2 fragments, as well as single chain antibodies (scFv), fusion proteins and other synthetic proteins which comprise the antigen-binding site of the antibody. Furthermore, the antibodies and fragments thereof may be humanised antibodies, for example as described in U.S. Pat. No. 239,400. Neutralizing antibodies, i.e., those which inhibit biological activity of the substance polypeptides, are especially preferred for diagnostics and therapeutics.

Antibodies may be produced by standard techniques, such as by immunisation with the substance of the invention or by using a phage display library.

Assay

Any one or more of appropriate targets—such as an amino acid sequence and/or nucleotide sequence—may be used for identifying an agent capable of modulating of NAD(P)H and/or NDO in any of a variety of drug screening techniques. The target employed in such a test may be free in solution, affixed to a solid support, borne on a cell surface, or located intracellularly. The abolition of target activity or the formation of binding complexes between the target and the agent being tested may be measured.

The assay of the present invention may be a screen, whereby a number of agents are tested. In one aspect, the assay method of the present invention is a high through put screen.

Techniques for drug screening may be based on the method described in Geysen, European Patent Application 84/03564, published on Sep. 13, 1984. In summary, large numbers of different small peptide test compounds are synthesized on a solid substrate, such as plastic pins or some other surface. The peptide test compounds are reacted with a suitable target or fragment thereof and washed. Bound entities are then detected—such as by appropriately adapting methods well known in the art. A purified target can also be coated directly onto plates for use in a drug screening techniques. Alternatively, non-neutralising antibodies can be used to capture the peptide and immobilise it on a solid support.

This invention also contemplates the use of competitive drug screening assays in which neutralising antibodies capable of binding a target specifically compete with a test compound for binding to a target.

Another technique for screening provides for high throughput screening (HTS) of agents having suitable binding affinity to the substances and may be based upon the method described in detail in WO 84/03564.

In a preferred aspect, the present invention provides a method for the high throughput screening for NAD(P)H-dependent oxidoreductase activity in microtitre plates.

It is expected that the assay methods of the present invention will be suitable for both small and large-scale screening of test compounds as well as in quantitative assays.

The present invention also provides the use of an assay method according to the present invention wherein the assay method is used to screen for mutant NDO(s) that may display useful properties—such as properties that could be exploited in chemical synthesis processes.

Reporters

A wide variety of reporters may be used in the assay methods (as well as screens) of the present invention with preferred reporters providing conveniently detectable signals (eg. by spectroscopy). By way of example, a reporter gene may encode an enzyme which catalyses a reaction which alters light absorption properties.

Other protocols include enzyme-linked immunosorbent assay (ELISA), radioimmunoassay (RIA) and fluorescent activated cell sorting (FACS). A two-site, monoclonal-based immunoassay utilising monoclonal antibodies reactive to two non-interfering epitopes may even be used. These and other assays are described, among other places, in Hampton R et al (1990, Serological Methods, A Laboratory Manual, APS Press, St Paul Minn.) and Maddox D E et al (1983, J Exp Med 15 8:121 1).

Examples of reporter molecules include but are not limited to (galactosidase, invertase, green fluorescent protein, luciferase, chloramphenicol, acetyltransferase, (glucuronidase, exo-glucanase and glucoamylase. Alternatively, radiolabelled or fluorescent tag-labelled nucleotides can be incorporated into nascent transcripts which are then identified when bound to oligonucleotide probes.

By way of further examples, a number of companies such as Pharmacia Biotech (Piscataway, N.J.), Promega (Madison, Wis.), and US Biochemical Corp (Cleveland, Ohio) supply commercial kits and protocols for assay procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. No. 3,817,837; U.S. Pat. No. 3,850,752; U.S. Pat. No. 3,939,350; U.S. Pat. No. 3,996,345; U.S. Pat. No. 4,277,437; U.S. Pat. No. 4,275,149 and U.S. Pat. No. 4,366,241.

Host Cells

In a preferred aspect, the biological system of the present invention is a cell—otherwise called a "host cell". The host cell in relation to the present invention includes any cell that could comprise the target for the agent of the present invention.

Thus, a further embodiment of the present invention provides host cells transformed or transfected with a polynucleotide that is or expresses the target of the present invention. Preferably said polynucleotide is carded in a vector for the replication and expression of polynucleotides that are to be the target or are to express the target. The cells will be chosen to be compatible with the said vector and may for example be prokaryotic (for example bacterial), fungal, yeast or plant cells.

The gram negative bacterium *E. coli* is widely used as a host for heterologous gene expression. However, large amounts of heterologous protein tend to accumulate inside the cell. Subsequent purification of the desired protein from the bulk of *E. coli* intracellular proteins can sometimes be difficult.

In contrast to *E. coli*, bacteria from the genus *Bacillus* are very suitable as heterologous hosts because of their capability to secrete proteins into the culture medium. Other bacteria suitable as hosts are those from the genera *Streptomyces* and *Pseudomonas*.

Depending on the nature of the polynucleotide encoding the polypeptide and/or the desirability for further processing of the expressed protein, eukaryotic hosts such as yeasts or other fungi may be preferred. In general, yeast cells are preferred over fungal cells because they are easier to manipulate.

However, some proteins are either poorly secreted from the yeast cell, or in some cases are not processed properly (e.g. hyperglycosylation in yeast). In these instances, a different fungal host organism should be selected.

Examples of suitable expression hosts within the scope of the present invention are fungi such as *Aspergillus* species (such as those described in EP-A-0184438 and EP-A-0284603) and *Trichoderma* species; bacteria such as *Bacillus* species (such as those described in EP-A-0134048 and EP-A-0253455), *Streptomyces* species and *Pseudomonas* species; and yeasts such as *Kluyveromyces* species (such as those described in EP-A-0096430 and EP-A-0301670) and *Saccharomyces* species. By way of example, typical expression hosts may be selected from *Aspergillus niger, Aspergillus niger* var. *tubigenis, Aspergillus niger* var. *awamori, Aspergillus aculeatis, Aspergillus nidulans, Aspergillus orvzae, Trichoderma reesei, Bacillus subtilis, Bacillus licheniformis, Bacillus amyloliquefaciens, Kluyveromyces lactis* and *Saccharomyces cerevisiae.*

The use of suitable host cells—such as yeast, fungal and plant host cells—may provide for post-translational modifications (e.g. myristoylation, glycosylation, truncation, lapidation and tyrosine, serine or threonine phosphorylation) as may be needed to confer optimal biological activity on recombinant expression products of the present invention.

Another form of host cell could be an insect cell. Here, reference may be made to Baculovirus Expression Vectors: A Laboratory Manual by David R. O'Reilly, Lois Miller, Verne A. Luckow (Oxford Univ Press; ISBN: 0195091310).

Organism

The term "organism" in relation to the present invention includes any organism that could comprise the target according to the present invention and/or products obtained therefrom. Examples of organisms may include a fungus, yeast or a plant.

The term "transgenic organism" in relation to the present invention includes any organism that comprises the target according to the present invention and/or products obtained.

Transformation of Host Cells/Host Organisms

As indicated earlier, the host organism can be a prokaryotic or a eukaryotic organism. Examples of suitable prokaryotic hosts include *E. coli* and *Bacillus subtilis*. Teachings on the transformation of prokaryotic hosts is well documented in the art, for example see Sambrook et al (Molecular Cloning: A Laboratory Manual, 2nd edition, 1989, Cold Spring Harbor Laboratory Press) and Ausubel et al., Current Protocols in Molecular Biology (1995), John Wiley & Sons, Inc.

If a prokaryotic host is used then the nucleotide sequence may need to be suitably modified before transformation—such as by removal of introns.

In another embodiment the transgenic organism can be a yeast. In this regard, yeast have also been widely used as a vehicle for heterologous gene expression. The species *Saccharomyces cerevisiae* has a long history of industrial use, including its use for heterologous gene expression. Expression of heterologous genes in *Saccharomyces cerevisiae* has been reviewed by Goodey et al (1987, Yeast Biotechnology, D R Berry et al, eds, pp 401–429, Allen and Unwin, London) and by King et al (1989, Molecular and Cell Biology of Yeasts, E F Walton and G T Yarronton, eds, pp 107–133, Blackie, Glasgow).

For several reasons *Saccharomyces cerevisiae* is well suited for heterologous gene expression. First, it is non-pathogenic to humans and it is incapable of producing certain endotoxins. Second, it has a long history of safe use following centuries of commercial exploitation for various purposes. This has led to wide public acceptability. Third, the extensive commercial use and research devoted to the organism has resulted in a wealth of knowledge about the genetics and physiology as well as large-scale fermentation characteristics of *Saccharomyces cerevisiae*.

A review of the principles of heterologous gene expression in *Saccharomyces cerevisiae* and secretion of gene products is given by E Hinchcliffe E Kenny (1993, "Yeast as a vehicle for the expression of heterologous genes", Yeasts, Vol 5, Anthony H Rose and J Stuart Harrison, eds, 2nd edition, Academic Press Ltd.).

Several types of yeast vectors are available, including integrative vectors, which require recombination with the host genome for their maintenance, and autonomously replicating plasmid vectors.

In order to prepare the transgenic *Saccharomyces*, expression constructs are prepared by inserting the nucleotide sequence into a construct designed for expression in yeast. Several types of constructs used for heterologous expression have been developed. The constructs contain a promoter active in yeast fused to the nucleotide sequence of the present invention, usually a promoter of yeast origin, such as the GAL1 promoter, is used. Usually a signal sequence of yeast origin, such as the sequence encoding the SUC2 signal peptide, is used. A terminator active in yeast ends the expression system.

For the transformation of yeast several transformation protocols have been developed. For example, a transgenic *Saccharomyces* according to the present invention can be prepared by following the teachings of Hinnen et al (1978, Proceedings of the National Academy of Sciences of the USA 75, 1929); Beggs, J D (1978, Nature, London, 275, 104); and Ito, H et al (1983, J Bacteriology 153, 163–168).

The transformed yeast cells are selected using various selective markers. Among the markers used for transformation are a number of auxotrophic markers such as LEU2, HIS4 and TRP1, and dominant antibiotic resistance markers such as aminoglycoside antibiotic markers, eg G418.

Another host organism is a plant. The basic principle in the construction of genetically modified plants is to insert genetic information in the plant genome so as to obtain a stable maintenance of the inserted genetic material. Several techniques exist for inserting the genetic information, the two main principles being direct introduction of the genetic information and introduction of the genetic information by use of a vector system. A review of the general techniques may be found in articles by Potrykus (Annu Rev Plant Physiol Plant Mol Biol [1991] 42:205–225) and Christou (Agro-Food-Industry Hi-Tech Mar./Apr. 1994 17–27). Further teachings on plant transformation may be found in EP-A-0449375.

Host cells transformed with the nucleotide sequence may be cultured under conditions suitable for the expression of the encoded protein. The protein produced by a recombinant cell may be displayed on the surface of the cell. If desired, and as will be understood by those of skill in the art, expression vectors containing coding sequences can be designed with signal sequences which direct secretion of the coding sequences through a particular prokaryotic or eukaryotic cell membrane. Other recombinant constructions way join the coding sequence to nucleotide sequence encoding a polypeptide domain which will facilitate purification of soluble proteins (Kroll D J et al (1993) DNA Cell Biol 12:441–53).

Therapy

The agents identified by the assay method of the present invention may be used as therapeutic agents—i.e. in therapy applications.

The term "therapy" includes curative effects, alleviation effects, and prophylactic effects.

The therapy may be on humans or animals.

Additional Biological Studies

If desired, the agents identified by the assay method of the present invention can be further investigated using other assay systems.

Pharmaceutical Compositions

It is also possible to provide a pharmaceutical composition comprising administering a therapeutically effective amount of the agent of the present invention and a pharmaceutically acceptable carrier, diluent or excipients (including combinations thereof).

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition may be formulated to be delivered using a mini-pump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be delivered by both routes.

Where the agent is to be delivered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

Pharmaceutical Combinations

The agent of the present invention may be administered with one or more other pharmaceutically active substances.

There is also included within the scope of the preferred embodiments of the present invention, combinations of an agent according to the present invention together with a supplementary therapeutic agent used for the purpose of auxiliary treatment.

In the above-described combinations of the present invention, the agent of the present invention and other therapeutic active agents may be administered in terms of dosage forms either separately or in conjunction with each other, and in terms of their time of administration, either serially or simultaneously. Thus, the administration of one component agent may be prior to, concurrent with, or subsequent to the administration of the other component agent(s).

Administration

Typically, a physician will determine the actual dosage which will be most suitable for an individual subject and it will vary with the age, weight and response of the particular patient. The dosages below are exemplary of the average case. There can, of course, be individual instances where higher or lower dosage ranges are merited.

The compositions of the present invention may be administered by direct injection. The composition may be formulated for parenteral, mucosal, intramuscular, intravenous, subcutaneous, intraocular or transdermal administration.

Depending upon the need, the agent may be administered at a dose of from 0.01 to 30 mg/kg body weight, such as from 0.1 to 10 mg/kg, more preferably from 0.1 to 1 mg/kg body weight.

By way of further example, the agents of the present invention may be administered in accordance with a regimen of 1 to 4 times per day, preferably once or twice per day. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The term "administered" includes delivery by viral or non-viral techniques. Viral delivery mechanisms include but are not limited to adenoviral vectors, adeno-associated viral (AAV) vectos, herpes viral vectors, retroviral vectors, lentiviral vectors, and baculoviral vectors. Non-viral delivery mechanisms include lipid mediated transfection, liposomes, immunoliposomes, lipofectin, cationic facial amphiphiles (CFAs) and combinations thereof. The routes for such delivery mechanisms include but are not limited to mucosal, nasal, oral, parenteral, gastrointestinal, topical, or sublingual routes.

The term "administered" includes but is not limited to delivery by a mucosal route, for example, as a nasal spray or aerosol for inhalation or as an ingestable solution; a parenteral route where delivery is by an injectable form, such as, for example, an intravenous, intramuscular or subcutaneous route.

For some applications, preferably the agent is administered orally.

General Recombinant DNA Methodology Techniques

Although in general the techniques mentioned herein are well known in the art, reference may be made in particular to Sambrook et al., Molecular Cloning, A Laboratory Manual (1989) and Ausubel et al., Short Protocols in Molecular Biology (1999) 4th Ed, John Wiley & Sons, Inc. PCR is described in U.S. Pat. No. 4,683,195, U.S. Pat. No. 4,800,195 and U.S. Pat. No. 4,965,188.

Preferred Assay

In a preferred aspect, we present a new method for screening in whole cells on microtitre plates for efficient substrate turnover by P450 BM3. The assay is based on the spectrophotometric and/or fluorometric detection of the product generated after treatment of $NADP^+$ with strong alkali (25, 26). This assay can be generalised for the screening of catalytically efficient variants of various oxidoreductases utilising NAD(P)H as cofactor (e.g. see Scheme 1 (see FIG. 9A) and Scheme 2 (see FIG. 9B)). The viability of the whole-cell assay is demonstrated by applying it to study the activity of the wild type P450 BM3 with three substrates, in parallel to studies on the purified enzyme. Among the natural fatty acid substrates of the P450 BM3 arachidonic acid (AA) and lauric acid (LA) were chosen because the first has been reported to be the one most rapidly hydroxylated by P450 BM3, while the second is slowly hydroxylated. On the other hand the anionic surfactant sodium dodecyl sulphate (SDS) was selected as a model for non-physiological substrates. SDS has been reported as substrate for P450 BM3 (27), however its binding and turnover by P450 BM3 have not been studied. Finally, the performance of the screening method was applied in a microtitre plate scale using whole cells, in order to test the activity of wild-type P450 BM3 against the polychlorinated alkane 1,1,2,2-tetrachloroethane (TCE) reported in the literature as P450 BM3 substrate (7).

The proposed assay offers a powerful tool for two important areas of applications:
(1) screening NAD(P)H-linked enzymatic activity of molecules of pharmacological (new potential drugs) and biotechnological (bioremediation and biosensing) interest (e.g. see Scheme 1);
(2) screening libraries of random mutants of NAD(P)H-dependent enzymes to allow design of new catalytic specificities of these enzymes (e.g. see Scheme 2).

SUMMARY

A method for screening for substrate turnover by NAD(P)H-dependent oxidoreductases is presented.

A preferred method is based on the detection of the product of NAD(P)H oxidation during substrate turnover by oxidoreductases in whole cells, and it has been demonstrated for cytochrome P450 BM3, the best model known so far for human P450 enzymes. The performance of the new method on whole cells has been tested on two natural substrates of the wild-type enzyme arachidonic (AA) and lauric (LA) acids, and a molecule with environmental significance, the anionic surfactant sodium dodecyl sulphate (SDS). Under the optimum experimental conditions the background signal given by cells expressing cytochrome P450 BM3, in the absence of added substrate was only 3% of the signal in the presence of the substrate. Control experiments have proven that this method is specifically detecting NADPH oxidation by substrate-bound P450 BM3. Moreover, the assay was adapted to a microtitre plate format and used to screen further agent candidates. Molecules among those studied were identified as substrates. The method was even able to select between isomers of certain candidate agents. All results found on the whole cells were verified and confirmed with the purified enzyme in an in vitro format.

The proposed assay offers a powerful tool for two important areas of applications:
(1) screening NAD(P)H-linked enzymatic activity of molecules of pharmacological (new potential drugs) and biotechnological (bioremediation and biosensing) interest (Scheme 1):
(2) screening libraries of random mutants of NAD(P)H-dependent enzymes to allow design of new catalytic specificities of these enzymes (Scheme 2).

EXAMPLES

The present invention will now be described by way of example only and with reference to the following Figures:

FIG. 1 which presents graphs

Figure 2:
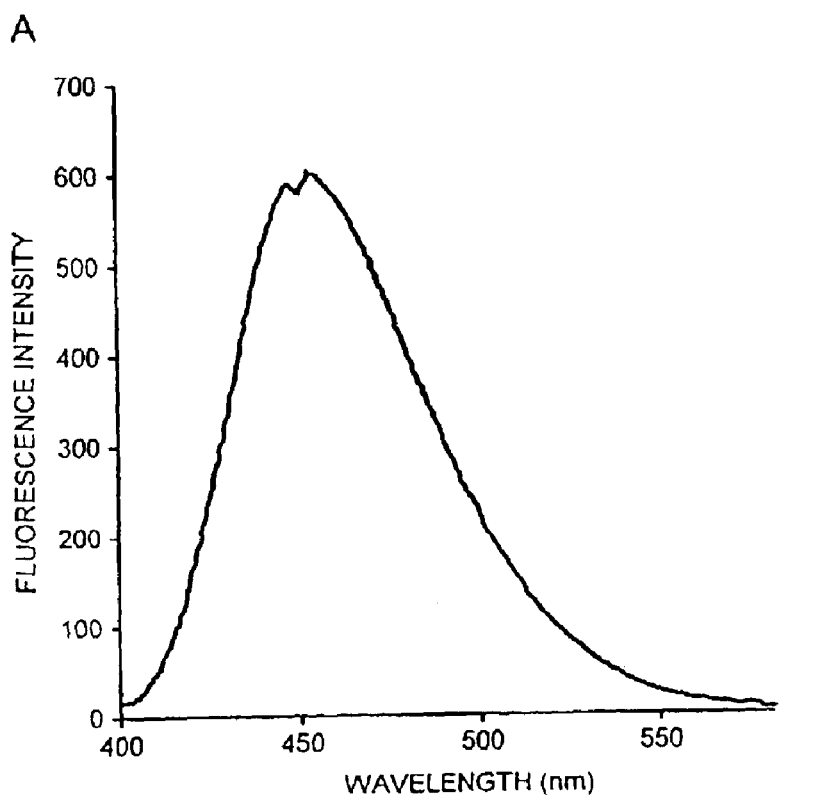
Figure 2:
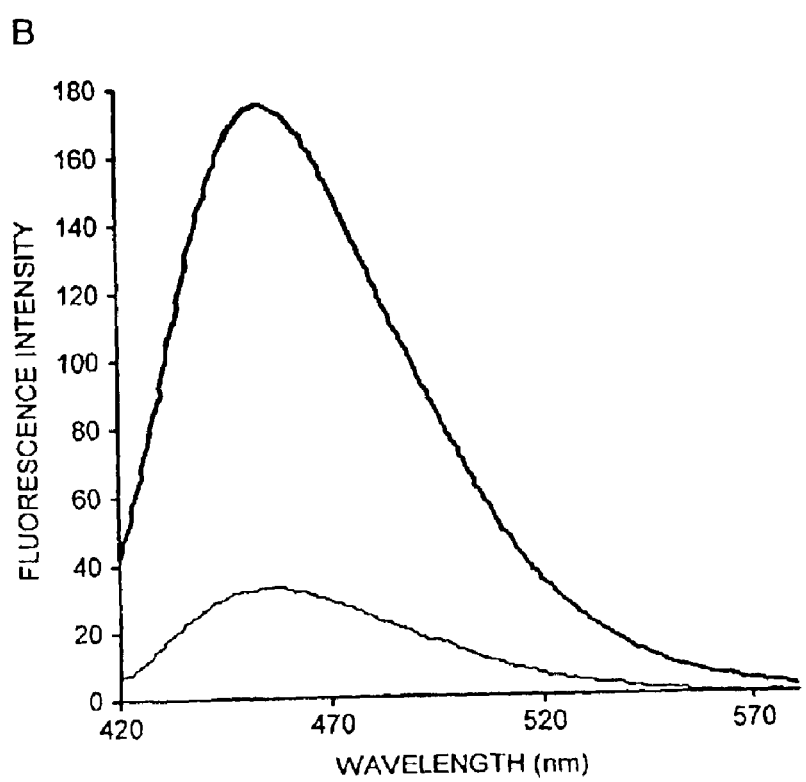

FIG. 2 which presents graphs

Figure 3:
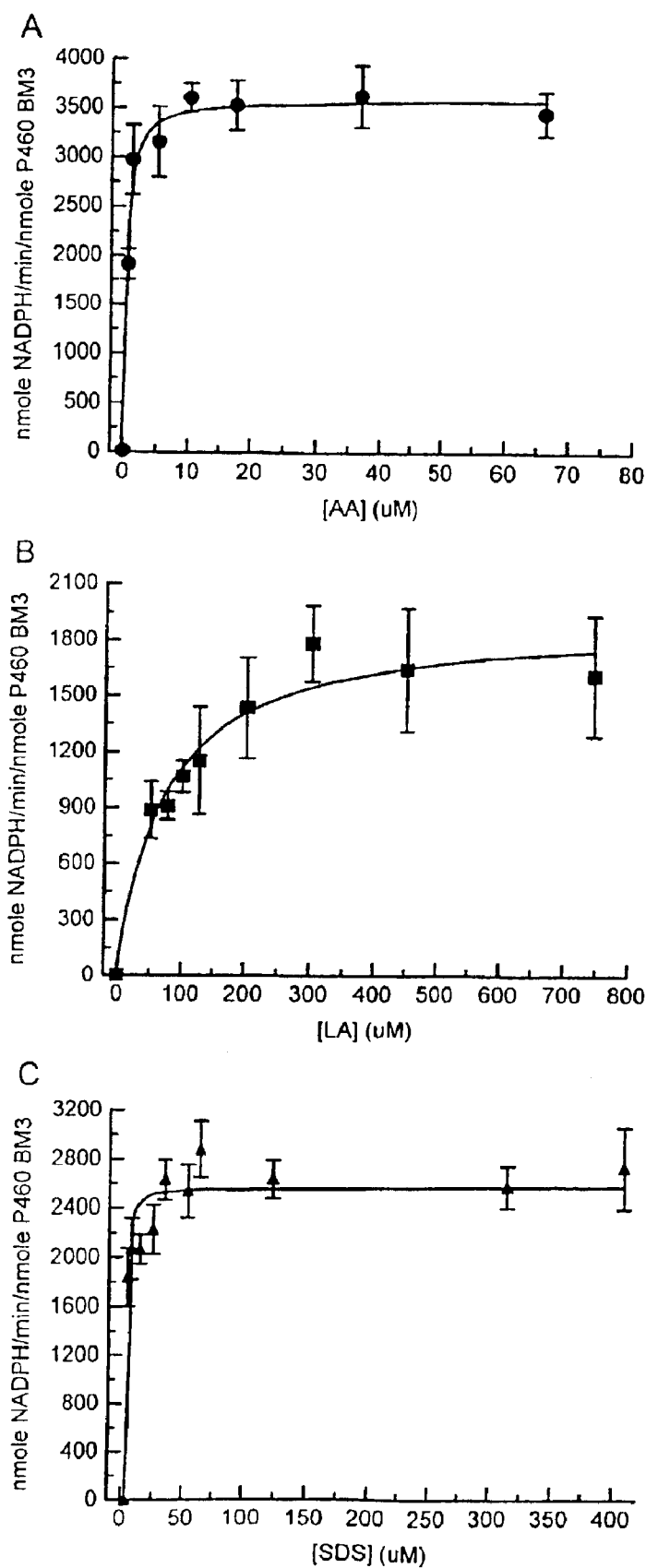

FIG. 3 which presents graphs

Figure 4:
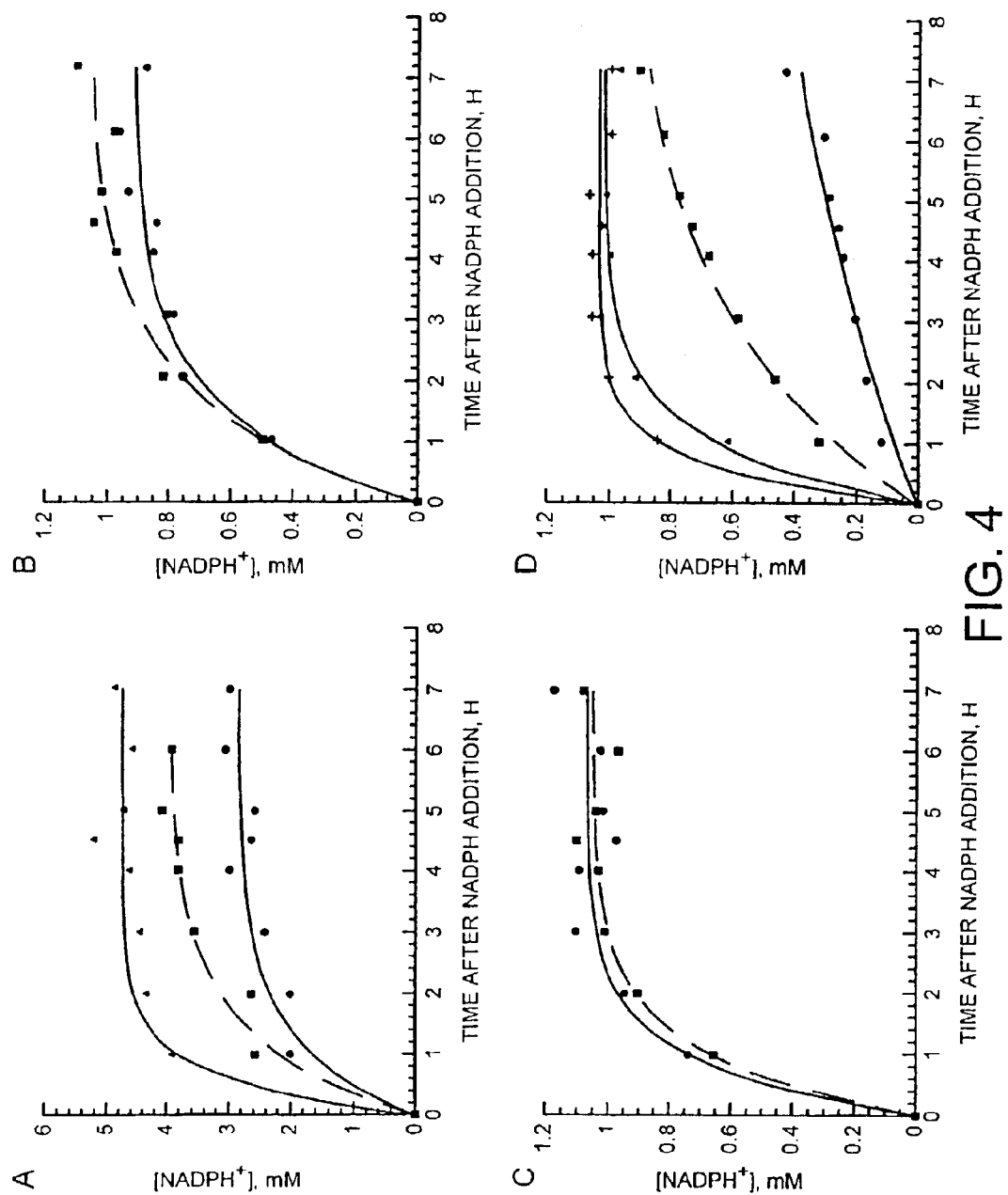

FIG. 4 which presents graphs

Figure 5:
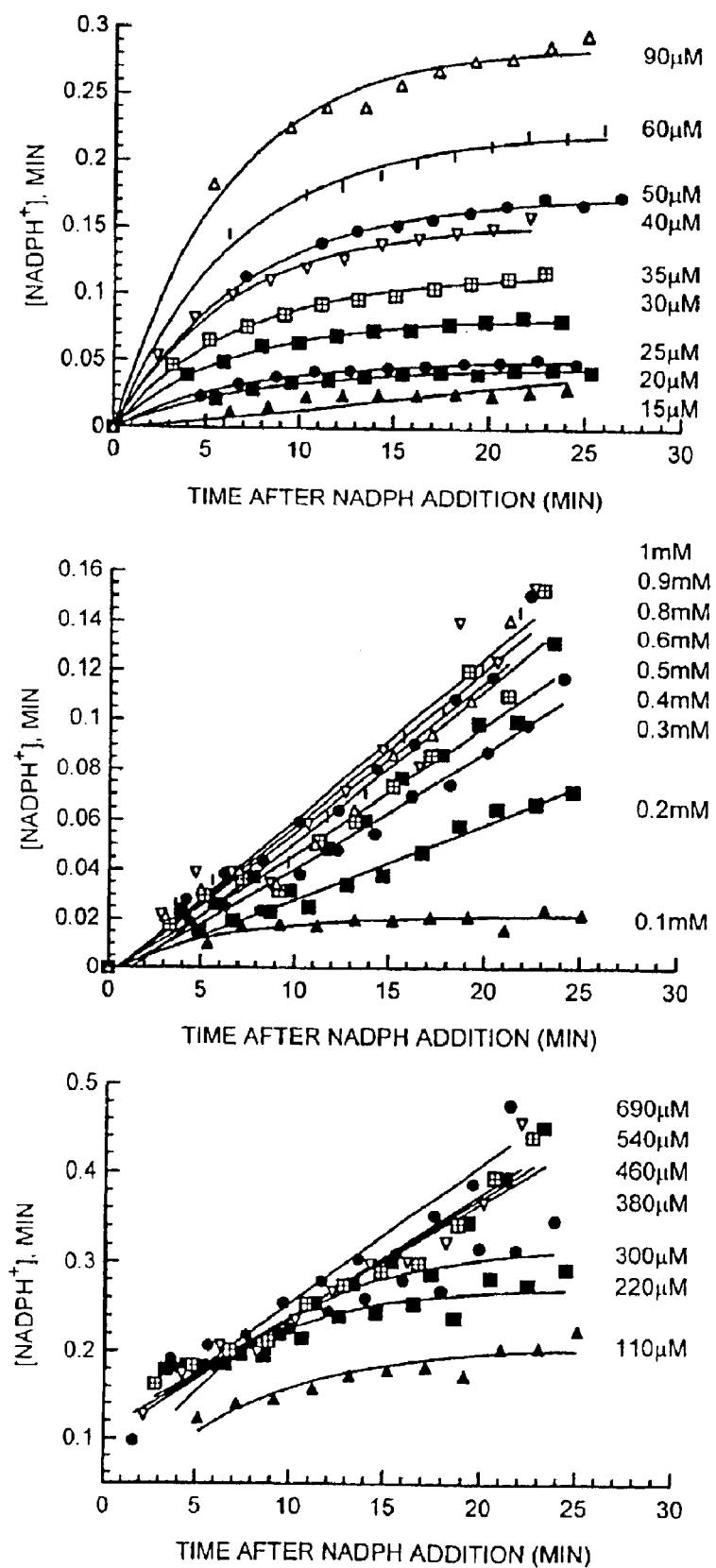

FIG. 5 which presents graphs

Figure 6:
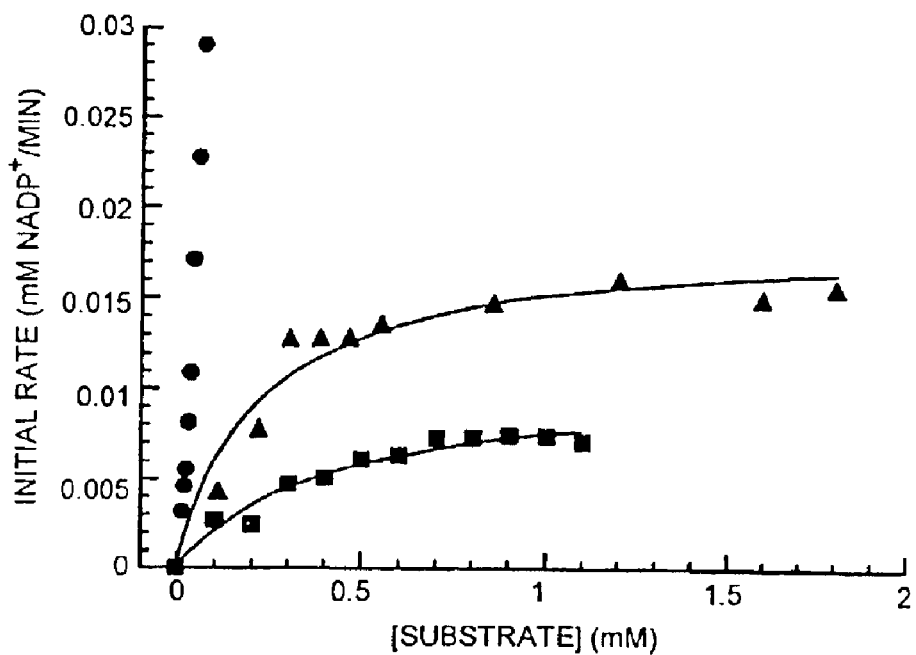

FIG. 6 which presents graphs

Figure 7:
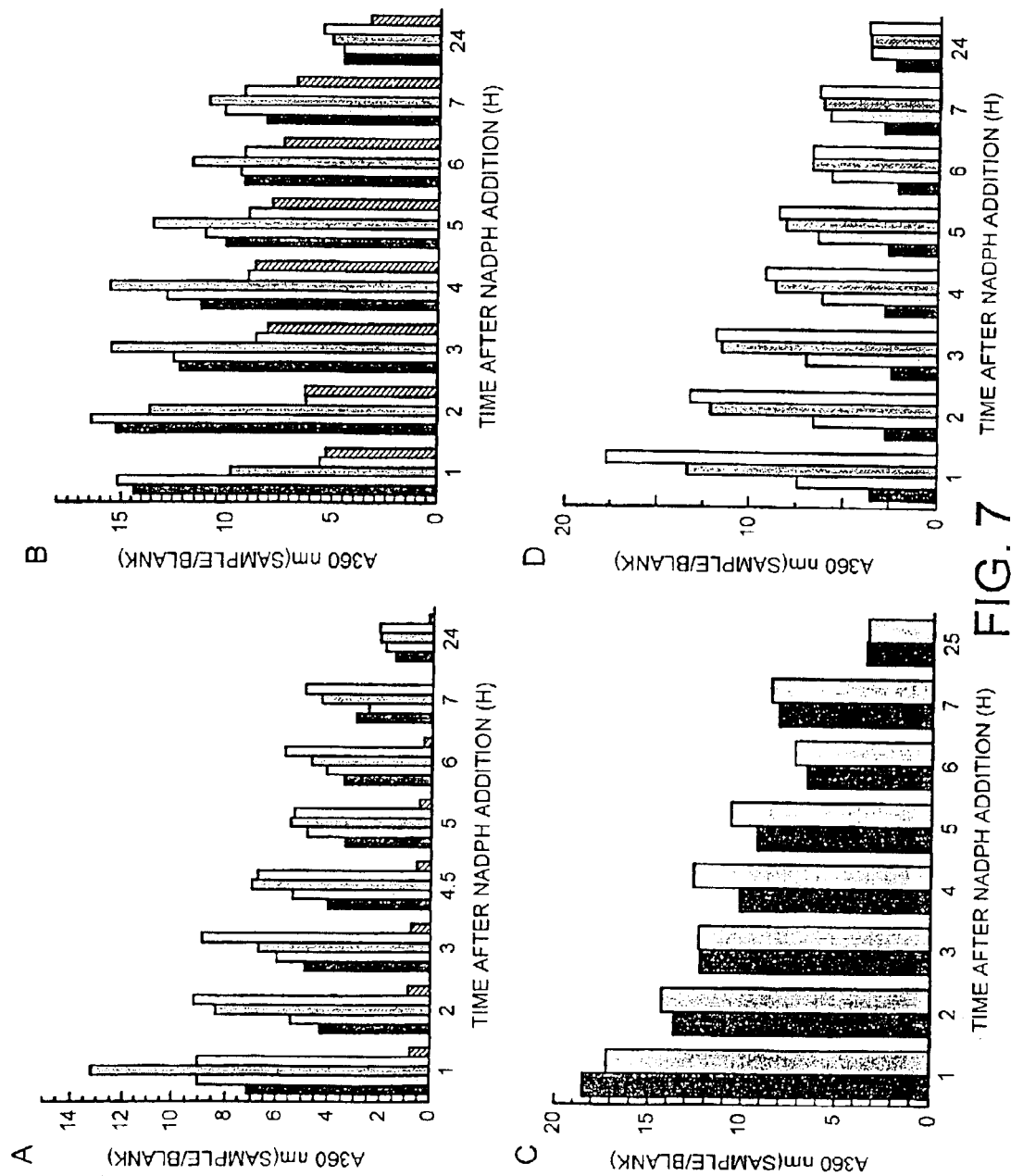

FIG. 7 which presents graphs

Figure 8:
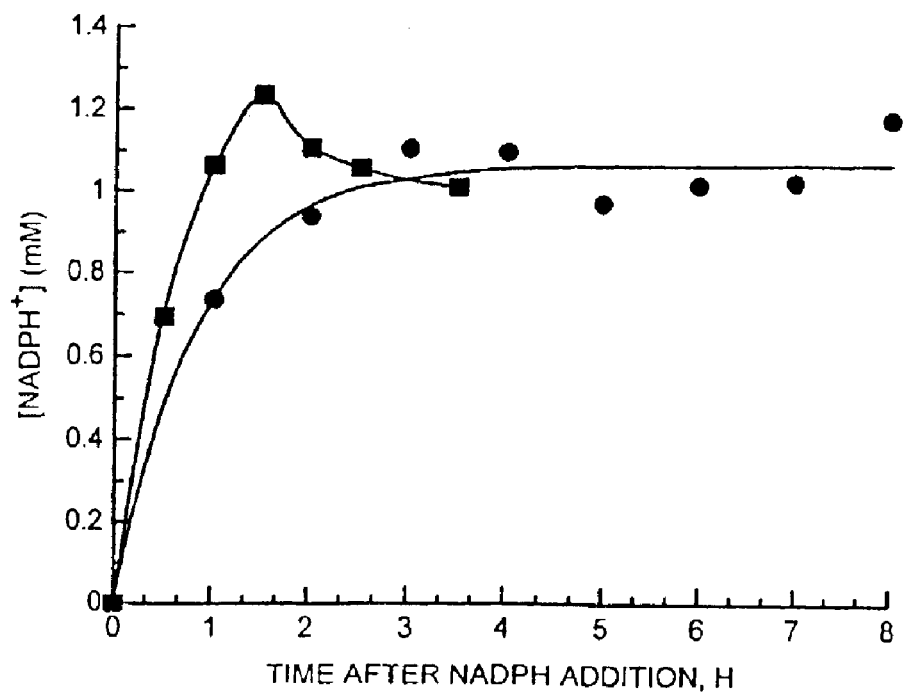

FIG. 8 which presents a graph

Figure 9:
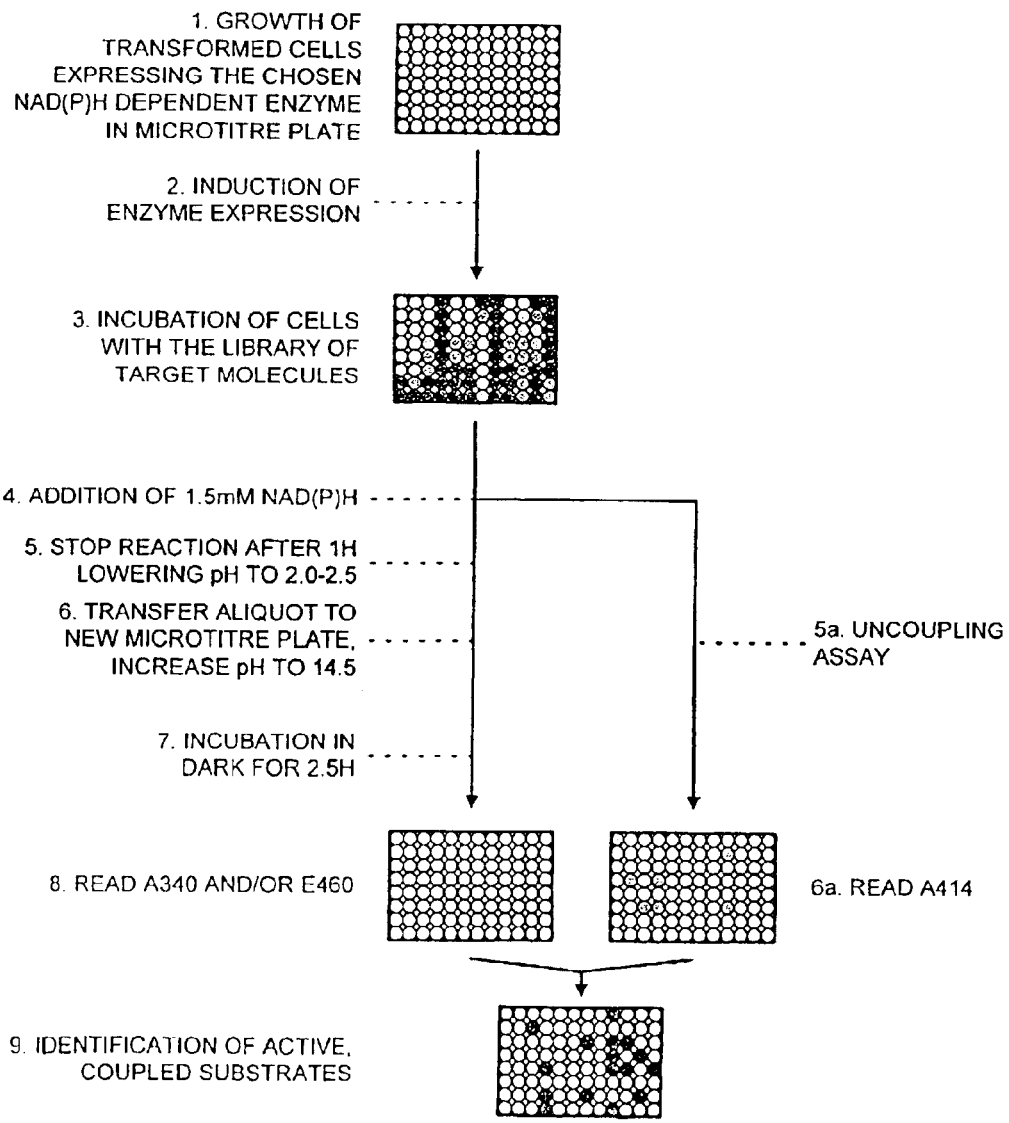

FIG. 9 which presents two schemes.

These Figures are now discussed in more detail.

FIG. 1. UV-visible spectra showing the formation of the alkali product of $NADP^+$ with purified P450 BM3 (A) and whole cells (B). (A). P450 BM3 (1.3 µM) (thick line), was saturated with lauric acid (1.5 mM) (thin line) and incubated with NADPH (570 µM). After all NADPH was consumed as judged from the disappearance of the 340 nm peak, the mixture was treated initially with acid and then with strong alkali, as described in the text. After formation of an intermediate product absorbing at 347 nm (dotted line), a stable product absorbing at 360 nm is formed (dashed line) (B). Formation of the alkali product of NADP+ with whole E.coli BL21(DE3) transformed with the plasmid expressing P450 BM3 in the absence of substrate (thin line) or in the presence of lauric acid (2.2 mM) (thick line spectrum). Cells were incubated with NADPH (1.5 mM) for 1 h 30 min.

FIG. 2. Fluoresence emission spectra of the alkali product formed in the experiment described in FIG. 1. by the purified P450 BM3 (A) and E.coli BL21(DE3) cells expressing P450 BM3 (B). In (B) the emission spectra at 1:10 dilution of whole E.coli BL21(DE3) cells expressing P450 BM3 in the absence of substrate (thin line) or in the presence of lauric acid (2.2 mM) (thick line spectrum) are shown. In both experiments excitation was at 360 nm, while the emission range was from 400 nm (or 420 nm) to 580 nm. The excitation and emission slit width was 2.5 nm and 8.0 nm respectively.

FIG. 3. Substrate-dependent NADPH oxidation by purified P450 BM3 incubated with (A) AA, (B) LA and (C) SDS. Data points are fitted to the Michaelis-Menten function. Error bars represent standard deviations from the mean of at least four measurements.

FIG. 4. Variation in the concentration of the A360 nm alkali product (expressed as NADP+ concentration) with time in BL21 (pT7Bm3Z) cells incubated with (A) AA at 50 $\mu$M (●), 100 $\mu$M (■), 170 $\mu$M (▲); (B) LA at 0.8 mM (●), 1.6 mM (■); (C) SDS at 0.75 mM (●), 1.5 mM (■) and (D) TCE at 1.0 mM (●), 2.0 mM (■), 4.0 mM (▲), 8.0 mM (+) relative to cells non-incubated with substrate. The data points were fitted to the exponential growth function. NADPH added was 1.5 mM. The absorbance of the alkali product is corrected for the blank absorbance.

FIG. 5. Variation in the A360 nm alkali product (expressed as NADP+ concentration) generated in the in-vivo assay, with time for various concentrations of substrates (as indicated to the right of the corresponding curve). The data points in (A) AA, (B) LA and (C) SDS were fitted either to the linear or to the exponential growth function. NADPH added was 1.5 mM. The absorbance of the alkali product is corrected for the blank absorbance.

FIG. 6. (A). Plots of initial rate (mM NADP+/min) of alkali product formation against substrate concentration for (●) AA, (■) LA and (▲) SDS generated in the in-vivo assay of FIG. 5. For those substrate concentrations of FIG. 5 that show an exponential growth behaviour already in the first 25 min of the reaction the initial rate was calculated by fitting the experimental data up to at least the first 20 min to a second order polynomial function. Otherwise the data of FIG. 5 were fitted to the linear function. The initial rates calculated were then fitted to the Michaelis-Menten function.

FIG. 7. Variation in the ratio of the A360 nm alkali product generated by BL21 (pT7Bm3Z) cells incubated with (A) AA at 50 $\mu$M (filled bars), 100 $\mu$M (horizontally-hatched bars), 170 $\mu$M (diagonally-hatched bars), 240 $\mu$M (open bars), 375 $\mu$M (grey bars); (B) LA at 0.8 mM (filled bars), 1.6 mM (horizontally-hatched bars), 2.04 mM (diagonally-hatched bars), 2.8 mM (open bars), 3.36 mM (grey bars): (C) SDS at 0.75 mM (filled bars), 1.5 mM (horizontally-hatched bars), and (D) TCE at 1.0 mM (filled bars), 2.0 mM (horizontally-hatched bars), 4.0 mM (diagonally-hatched bars), 8.0 mM (open bars), relative to cells non-incubated with substrate. NADPH added was 1.5 mM. The absorbance of the alkali product is corrected for the blank absorbance.

FIG. 8. Variation in the A360 nm alkali product (expressed as NADP+ concentration) generated by BL21 (pT7Bm3Z) cells incubated with SDS, with time. When several aliquots of SDS stock at 0.75 mM final concentration were added to the cells with a time lag of 20 min (■), the A360 nm product was increased (by about 35% at 1.5 h after NADPH addition) compared to cells incubated with 0.75 mM SDS (●). NADPH concentration in both cases 1.5 mM. The absorbance of the alkali product is corrected for the blank absorbance.

FIG. 9. A. Scheme illustrating the assay procedure in the case of screening a library of molecules against a NAD(P)H dependent enzyme. B. Scheme illustrating the assay procedure in the case of screening a library of mutants of a NAD(P)H dependent enzyme against a target molecule.

Experimental Protocol

P450 BM3 Expression and Purification. P450 BM3 was expressed from E.coli BL21(DE3) cells transformed with plasmid pT7Bm3Z carrying the P450 BM3 gene under the control of the T7 RNA polymerase promoter $\phi$10 (33). Expression and purification of P450 BM3 was carried out with minor alterations to the published protocols (34). E.coli BL21(DE3) cells freshly transformed with the pT7Bm3Z plasmid were grown overnight at 37° C. in 4 ml Luria-Bertani (LB)/ampicillin (120 $\mu$g/ml) medium. The next morning they were used to inoculate at 1:100 dilution 200 ml LB/ampicillin (120 $\mu$g/ml) medium. The cells were grown at 37° C. to an OD600 of about 1 and were then diluted 1:100 in LB/ampicillin (120 $\mu$g/ml) medium. After growth at 37° C. to an OD600 of about 1, P450 BM3 expression was induced by the addition of IPTG at 1.0–2.0 mM final concentration. The temperature was lowered to 35° C. and the growth was continued for 19.5 hours after induction, using vigorous agitation. Cells were harvested and lysed using French Press, the lysate was ultracentrifuged at 35,000 rpm at 4° C. for 1 h and the supernatant was loaded onto a Q-Sepharose column. A second anion exchange chromatography step followed (DEAE-Sepharose). The final P450 BM3 pool was concentrated by ultrafiltration and the buffer was exchanged into HEPES 50 mM pH 8.0. The enzyme was stored in this same buffer at −20° C. until further use.

Substrate Binding and NADPH Consumption Assays. Substrate binding was followed in a Hewlett-Packard 8452A diode array spectrophotometer, equipped with a Hewlett-Packard peltier temperature controller 89090 by monitoring the increase in the high spin band of the haem at 390 nm, upon titration with different substrates. The dissociation constant $K_d$ was calculated by fitting the obtained data to the equation $$[ES] = ((\Delta A_{390} \Delta A_{421})_{max} \cdot [S]_{free})/(K_d + [S]_{free})$$

where $$[ES] = (\Delta A_{390} \Delta A_{421})/(\Delta A_{392} \Delta A_{421})_{max} \cdot [P450\ BM3] \text{ and } [S]_{free} = [S]_{added} - [ES].$$

NADPH consumption was followed at 340 nm using a $\Delta\epsilon_{340} = 6.22$ mM$^{-1}$·cm$^{-1}$. Both assays were performed at 20° C. using P450 BM3 in 100 mM potassium phosphate buffer, pH 8.0. Reaction was initiated by addition to the substrate bound enzyme of NADPH to a final concentration of 130–150 $\mu$M. In the kinetics assay the rate constant $k_{cat}$ was calculated from the linear part of the decrease in A340 with time, which lasted at least for the first 4 sec. The enzyme concentration typically varied between 0.4 and 0.8 $\mu$M in the binding assay and between 8 and 25 nM in the catalytic assay. Substrate stock solutions were freshly prepared the day of the assay. Fatty acid stock solutions were in 50 mM potassium carbonate, SDS was easily dissolved in water, while TCE stock solutions were prepared in ethanol. If appropriate, stocks of candidate agents may be prepared in, for example, N,N-dimethylformamide just before the assay. During binding or kinetic studies the organic solvent concentration added to the protein solution did not exceed 1.1% v/v. The confidence interval for $K_d$ given in the results section is the mean±the standard deviation of at least four measurements, as calculated using the software Kaleidagraph. Similarly $k_{cat}$ was calculated by fitting data points to the Michaelis-Menten equation. Each data point is the mean of at least four measurements.

Hydrogen Peroxide Determination. Uncoupled reactions were determined by measuring the production of hydrogen peroxide during substrate turnover using the horseradish peroxidase (HRP)/2'2-Azino-di(3-ethyl-benzathiazoline-6-sulphonic acid) (ABTS) assay as described by Childs and Bardsley (31). The extinction coefficient at 414 nm of the radical cation of ABTS was calculated to 32.95 $mM^{-1}$ $cm^{-1}$, in accordance with the published value. The assay mixture composition was essentially similar to that utilised during the substrate-dependent NADPH consumption assay (20–30 nM P450 BM3 in 100 mM potassium phosphate buffer pH 8.0, 150 $\mu$M NADPH, and at least 1.7 times higher substrate concentration relative to NADPH concentration). When all NADPH was consumed (as judged from the disappearance of the 340 nm peak) the hydrogen peroxide produced was measured. Uncoupling in whole cells was measured following essentially the same assay in whole cells in 100 mM potassium phosphate buffer pH 8.0 incubated with substrate and NADPH as in the alkali method.

Development of the Alkali Product of $NADP^+$ (the Alkali Assay). The hydroxylating activity of whole cells expressing cytochrome P450 BM3 was measured in terms of $NADP^+$ production. $NADP^+$ was determined by treatment with strong alkali as described by Kaplan et al. (25, 26). The assay has been adapted in a microtitre plate format as follows. A single colony from freshly transformed E.coli BL21(pT7Bm3Z) cells was inoculated into 170 $\mu$l LB/ampicillin (120 $\mu$g/ml) in a microtitre plate well. Cells were grown to an $OD_{600}$~0.8 before being induced with 1 mM IPTG. After incubation at 37° C. for 16 hours after induction, the cells were harvested and washed once with 100 mM potassium phosphate buffer pH 8.0. The cell pellet was stored in the −20° C. freezer before running the alkali test within the next few days. The cell pellet was then resuspended at 1:1.3 dilution in 100 mM potassium phosphate buffer pH 8.0. to give an $OD_{600}$ of about 0.4, to which the substrate at the desired concentration was added (stock solutions of substrates as described for the binding and catalytic assays). A control consisting of cells in phosphate buffer added with the same amount of potassium carbonate solution or ethanol or N,N-dimethylformamide, without substrate was run for every sample. All samples were incubated at room temperature overnight. NADPH at 1.5 mM was then added to the samples and at 1 h after NADPH addition, an aliquot (typically 70 $\mu$l) was transferred in a new microtitre plate to which was added the same volume (typically 70 $\mu$l) of 0.3 M HCl, so that the final pH in the mixture is about 2. The aliquots were incubated for at least 10 min at room temperature, to ensure complete destruction of the remaining reduced NADPH. An aliquot (typically 70 $\mu$l) was then removed and transferred in a new microtitre plate with 280 $\mu$l of 9 M NaOH to yield a solution of a pH of about 14.8. The mixture was immediately mixed thoroughly and placed in the dark. The product was left to develop in dark for at least 2.5 h at room temperature, after which the absorbance at 360 nm or the emission at 455 nm ($\lambda_{ex}$=360 nm) was measured. It has to be noted here that the molarity and the absolute volumes of the solutions used in the assay are arbitrary and are defined depending on the concentration of $NADP^+$ expected in the reaction mixture, in such a way that the pH of the different incubation mixtures is within the accepted range (pH 1–2.5 for NADPH elimination; 14.5–15 for development of the alkali product). The extinction coefficient of the product formed by alkali treatment of $NADP^+$ at 360 nm was calculated to 4.85 $mM^{-1}·cm^{-1}$. Standard curve of $NADP^+$ yielded a linear response up to at least 0.45 mM $NADP^+$. The linear region in the fluorometer was found to be from at least 0.1 $\mu$M NADPH up to 8.5 $\mu$M NADPH.

Results and Discussion

The screening method presented in the paper is based on the detection of NAD(P)H consumption directly correlated with the turnover of cytochrome P450 BM3 heterologously expressed in BL21(DE3) E.coli cells. The product of NADPH oxidation is detected via the generation of a stable fluorescent product obtained by treatment with strong alkali (alkali product). The formation of the alkali product in the presence of purified P450 BM3 (1.3 $\mu$M) with saturating lauric acid (1.5 mM) and NADPH (570 $\mu$M) was followed spectrophotometrically and the results are shown in FIG. 1A. The spectrum of the purified non-bound and laurate-saturated P450 BM3 is given by the thick and thin line respectively. Treatment of this mixture with acid, to eliminate possible residual NADPH, followed by strong alkali, as described in the experimental section, resulted within the first 15 min of the reaction in the dotted line spectrum of FIG. 1A with a peak at 347 nm corresponding to an intermediate. This was fully converted after 2.5 h at room temperature into the stable fluorescent product at 360 nm shown by the dashed line spectrum. This product corresponds to the alkali fluorescent product previously observed (25, 26), and its fluorescence emission spectrum upon excitation at 360 nm is shown in FIG. 2A. The formation of the alkali product was then investigated on whole E.coli BL21 (DE3) cells expressing the P450 BM3 enzyme as described in the experimental section. Cells were incubated with lauric acid (2.2 mM) and NADPH (1.5 mM) and treated in the same way as in the in vitro experiment described above. The absorbance spectrum of the alkali product generated in the whole cells experiment is shown in FIG. 1B (thick line). The fluorescence emission spectrum of the same sample is given in FIG. 2B (thick line). Control experiments with the same cells treated with the procedure, but without addition of substrate resulted in the thin line absorbance spectrum of FIG. 1B, where the alkali product is present in negligible quantities. These data confirmed that the generation of the alkali product is related to P450 BM3 turnover in the presence of substrate. The emission spectrum of the same control is given in FIG. 2B (thin line). The background fluorescence of cells not incubated with NADPH was negligible compared to the sample signal. Moreover further control experiments were carried out in order to demonstrate the specific detection of the P450 BM3 activity in whole cells. E.coli BL21(DE3) cells non-transformed, or transformed with different plasmids of the pT7-7 vector expressing the haem domain alone of P450 BM3, or flavodoxin from Desulfovibrio vulgaris or cytocrome c peroxidase gave a much lower signal due to background metabolic NADPH oxidation. NADPH oxidation by oxygen dissolved in the reaction buffer was found to be negligible within the time scale of the experiment.

In order to test the efficiency of the screening method presented in this work, the activity of P450 BM3 was tested in parallel on whole E.coli BL21(DE3) cells expressing P450 BM3 (in-vivo assay) as well as on purified P450 BM3 (in vitro assay). The P450 BM3 activity was assessed by both the in vitro and in vivo methods on different groups of molecules selected on the basis of their structure, the enzyme turnover efficiency, or their significance as environmental pollutants or as potential drugs. In the experimental approach, molecules known to be substrates for P450 BM3 were characterised in their interaction with the purified enzyme, followed by tests in the in vivo method. On the other hand unknown substrates were tested in vivo first, and the outcome of this experiments was confirmed in detailed in vitro experiments. The chosen molecules were the physiological long-chain fatty acid substrates (AA high efficiency, LA low efficiency), the non-physiological long-chain anionic surfactant SDS (medium efficiency), and non-physiological organic molecules of variable bulkiness, either of environmental significance (TCE) or with potential pharmaceutical applications.

Among the molecules listed above the known substrates of P450 BM3, namely AA, LA and SDS were extensively studied both in vitro and in vivo. Substrate-dependent NADPH oxidation by purified P450 BM3 investigated using a well established spectrophotometric technique revealed a Michaelis-Menten behaviour for AA, LA and SDS, as shown in FIG. 3. It has to be noted that in any case the rate of NADPH consumption by the substrate-free P450 BM3 was found to be 2.5–5% that of the substrate-bound enzyme. The binding and kinetic parameters of these molecules are summarised in Table 1. For all of the substrates the extent of uncoupling of P450 BM3 from substrate hydroxylation was also determined using the purified enzyme, by the horseradish peroxidase (HRP)/2'2-Azino-di(3-ethyl-benzathiazoline-6-sulphonic acid) (ABTS) assay (31) and was found to be negligible (Table 1).

ment after NADPH addition and the concentration of the substrate added. A systematic study of the effects of these parameters on the assay was carried out also on BL21(DE3) cells transformed with the pT7Bm3Z plasmid expressing cytochrome P450 BM3. Whole cells were incubated without (blank) and with different levels of substrate (sample) and absorbance measurements at 360 nm (A360) were made at different times (FIG. 4). The exponential curves of FIG. 4 indicate that the assay developed in this work is depicting accurately the enzymatic reaction occurring in whole-cells expressing P450 BM3 upon incubation with substrate and administration of NADPH. The initial rate of the reaction is dependent upon the substrate concentration, while the time at which the plateau of the curve is reached depends on the efficiency of the substrate turnover. For example in the case of SDS at substrate concentration of about 0.8 mM the plateau of the exponential is reached at 3.5 h whilst for the same concentration of LA the plateau is reached after 7 h, indicating that SDS is more efficiently turned over than LA. A decrease in the A360 signal of the samples was observed at 24 h after NADPH addition suggesting that between 7 and 24 h after NADPH addition, the $NADP^+$ production by the cells was ceased due to substrate exhaustion. After that point the levels of $NADP^+$ dropped probably due to the $NADP^+$ consumption and/or reduction by other metabolic functions. The same set of experiments in whole cells was performed in a smaller time scale (~0–25 min after NADPH addition) in order to finely define the initial rate of the alkali fluorescent product formation and the data are shown in FIG. 5. Once more the order of the efficiency of turnover of the three substrates is verified. The more efficient a substrate is, the shorter is the linear phase of NADPH oxidation for the same range of substrate concentration. Thus at LA concentrations higher than 200 $\mu$M the linear region was found in the first 25 min, while in the case of SDS it was found at concentrations higher than 300 $\mu$M. Finally for arachidonic acid it was not possible to catch the linear phase due to limitations in the concentration range that could be used (see below).

TABLE 1

Kinetic and binding parameters of known substrates of cytochrome P450 BM3 calculated on the purified enzyme (in vitro) or on whole cells following the alkali assay (in vivo).

| | In vitro assay | | | | In vivo assay | | |
|---|---|---|---|---|---|---|---|
| Substrate | $K_d$ ($\mu$M) | $K_M$ ($\mu$M) | $k_{cat}$ (mole NADPH/ min/mole P450) | % $H_2O_2$ | A360/ E455 signal | $V_{max}$ (nM $NADP^+$/ min) | R |
| AA | $10^{-7}$ M range | 0.37 ± 0.07 | 3570 ± 88 | 0.11 | ✓ | n.d. | S |
| LA | 134.7 ± 38.2 | 67.8 ± 14.5 | 1928 ± 114 | 0.66 | ✓ | 10.26 ± 0.87 | S |
| SDS | 11.5 ± 3.7 | 0.51 ± 0.12 | 2605 ± 61 | 0.63 | ✓ | 18.19 ± 1.12 | S |
| TCE | 4009.2 ± 829.9 | 7960 ± 2041 | 5133.5 ± 641.3 | 0 | ✓ | | S |
| *n-hexane | n.o. | n.o. | n.o. | | × | | N | n.o.: not observed./n.d.: not determined
S: substrate; N: no-interaction
*n-hexane was used as a negative control.
The symbol ✓ denotes the observation of a signal while the symbol × the absence of a signal.
R = Remark Data from FIG. 3 show how the different substrates studied are hydroxylated with different efficiencies by the purified enzyme. It follows that depending on the substrate investigated, the level of the generated signal by the alkali treatment of $NADP^+$ measured in the assay on whole cells will vary upon the nature of the substrate, time of measure- When the initial rate of AA, LA, and SDS oxidation was plotted against substrate concentration a Michaelis-Menten-type curve was obtained as shown in FIG. 6. Due to the relatively high toxicity of AA to E.coli BL21(DE3) cells it was not possible to draw such a curve for AA, since only few points at very low substrate concentrations could be obtained. The kinetic parameters determined following the substrate-dependent NADPH oxidation with time in the whole-cell assay are given in Table 1. For all the three substrates the extent of uncoupling of P450 BM3 from substrate hydroxylation was also determined in a whole-cell assay. This was essentially an adaptation of the hydrogen peroxide quantification method of HRP with ABTS described for the experiments carried out on purified enzyme. In accordance to the assay on purified P450 BM3 none of the three substrates was found to divert electrons from substrate hydroxylation.

In order to find the optimal conditions for the production of the alkali product, different concentrations of substrates and different incubation times with whole cells were tested. The results are shown in FIG. 7. The plot of the observed ratio of the sample A360 signal/blank signal with time against a period of 7 h (FIG. 7) shows that the time at which the maximum ratio appears depends both on the concentration of substrate, as well as on the efficiency of its turnover by the enzyme. FIG. 7 indicates that the higher the catalytic efficiency of the enzyme for the substrate, the earlier the maximum ratio will occur at a given substrate concentration. The higher the concentration of a given substrate the later the maximum ratio should appear, since it is known that upon incubation of the non-bound P450 BM3 with NADPH the enzyme is within 20 min fully converted from a high activity into a low activity form (32). According to the results obtained from these observations, as shown by the data of FIG. 7, measurement at 1 h after NADPH addition should ensure a selection for highly efficient substrates when screening libraries of molecules against P450 BM3 and for highly efficient variants in the case of screening of random mutants of P450 BM3.

The potential lethal effect that high concentrations of substrate may have on whole cells (as in the case of arachidonic acid at concentrations higher than 170 µM, FIG. 7A.) can be overcome without loss of sensitivity by successive small additions of substrate. The increase of the A360 signal with subsequent additions of SDS to whole cells expressing P450 BM3 is reported in FIG. 8, where it can be observed how the increase in the absorbance becomes limited by the NADPH concentration. At 1.5 h after NADPH addition, when SDS is supplied periodically to the cells an increase of about 45% in the NADP$^+$ production is seen, which should correspond to a ratio of sample A360 signal/ blank signal of about 30. Thus, under the conditions used, the 30-fold difference in the observed signal between the substrate-bound and—free signal should allow the distinction of one active enzyme variant in a pool of 10.

These observations indicate that the screening assay using whole cells is suitable to select for positive enzymes and/or for potential new substrates. This may offer a great potential of a high throughput screening assay for novel potential drugs. This hypothesis was tested by setting up a test in a microtitre plate scale to study the potential interaction of six candidate agents with P450 BM3 in vivo. The candidate agents were screened for turnover by wild type cytochrome P450 BM3. The experimental procedure is illustrated in Scheme 1. The test was performed efficiently and rapidly on E.coli BL21(DE3) cells expressing P450 BM3. Some among them have given a positive absorbance and fluorescence signal of NADP$^+$ formation. The microtitre plate assay was also applied to study the interaction of a molecule of environmental significance, the polychlorinated alkane 1,1,2,2-tetrachloroethane with P450 BM3. Since the assay described depends on monitoring the rate of NADPH oxidation, rather than on the formation of the product of the catalysis, there exists the possibility that a substrate/ uncoupler is detected rather that an efficiently metabolised substrate. Thus the positive substrates identified were tested by the whole-cell HRP-ABTS assay. In order to test the performance of the rapid high throughput screening method, the interaction of all molecules tested with purified P450 BM3 was studied in vitro. The results obtained from the in vitro tests confirmed those obtained in vivo.

In conclusion the viability and efficiency of the screening assay proposed have been demonstrated. The assay is quite easy and presents the advantage that it is non-specific, since it can be applied to screen not only any P450 enzyme co-expressed with its reductase individually or as a fusion protein, but also any oxidoreductase in general that utilises NAD(P)H as a cofactor. It has to be noted that NADPH and NADH behave in exactly the same way in strong acid and alkali; that means that the assay should be equally efficient for enzymes using NADH as cofactor. It has been demonstrated that the assay can be used for screening for novel substrates of an oxidoreductase, distinguishing between uncouplers and substrates. It has also been demonstrated that it has the potential to be used for screening for efficient variants of a library of random mutants of a NADPH-dependent oxidoreductase.

Examples Summary

As indicated above, the use of combinatorial methods in both chemistry and biochemistry over the last few years has generated an enormous number of (bio)molecules of pharmaceutical (drugs) and biotechnological (biocatalysts) interest. The ability to effectively identify active molecules in random libraries relies on the availability of a screening method able to select the positive variants or derivatives, that can be further characterised and commercialised. An ideal, general screening method would be able to select the positive targets from a random library of molecules/ substrates tested against a specific binding protein/enzyme, as well as to select positive, active variants of a random library of binding proteins/enzymes against a specific target molecule/substrate.

The invention presented here deals with a method able to achieve the above. The method is based on the detection of either NAD(P)H consumption or generation in whole cells expressing a NAD(P)H-dependent target enzyme. NAD(P)H is a ubiquitous cofactor required by many oxidoreductases of biotechnological interest. The ability to detect substrate specific NAD(P)H consumption or production in whole cells, using a simple assay with cheap reagents in a microtitre plate format is a powerful tool for screening large random libraries of potential substrates against a target enzyme and/or libraries of enzyme mutants against a target substrate. The assay is based on the spectrophotometric detection of a stable fluorescent product of NADP$^+$ generated by treatment with alkali, as shown in the scheme below:

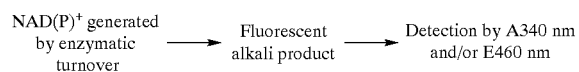

The performance and suitability of the screening method has been tested on cytochrome P450 BM3, the best model known for the large family of human P450 enzymes, that are central to pharmacodynamic studies of potential new drugs. This application is important for the pharmaceutical field. Moreover, the ability to produce random mutants of this monooxygenase able to degrade various substrates of environmental importance has relevant implications in the area of bioremediation and biosensing. The new method has been tested using whole *E.coli* cells expressing P450 BM3, with two natural substrates of the wild-type enzyme, arachidonic (AA) and lauric (LA) acids, and two molecules with environmental significance, the anionic surfactant sodium dodecyl sulphate (SDS) and 1,1,2,2-tetrachloroethane (TCE). Under the optimum experimental conditions the background signal given by cells expressing cytochrome P450 BM3, in the absence of added substrate was only 3% of the signal in the presence of substrate. Control experiments have proven that this method is specifically detecting NADPH oxidation linked to the target enzyme. Moreover, the assay was adapted to a microtitre plate format.

The proposed assay offers a powerful tool for two important areas of applications:

- screening NAD(P)H-linked enzymatic activity of molecules of pharmacological (new potential drugs) and biotechnological (bioremediation and biosensing) interest is (e.g. see Scheme 1):
- the assay can be used for all enzymes consuming and generating NADPH and NADH (in the former case the procedure is as in scheme 1, in the latter case the un-reduced NAD(P)+ is eliminated by increasing the pH to 11.7–12.3 without generating the fluorescent alkali product. The NAD(P)H target of the assay is then oxidised to NAD(P)+ by hydrogen peroxide and the NAD(P)+ is detected by treatment with NaOH to pH 15 to generate the fluorescent alkali product;
- the assay can be adapted to be used with all cells able to express the target NAD(P)H-dependent enzyme of choice;
- the assay can be used with P450 enzymes, in particular with the P450 BM3, that is a model for the human enzymes, hence an important test for pharmacodynamic screening;
- the wide substrate specificity of P450 offers a good test for ability of degradation of various pollutants;
- screening libraries of random mutants of NAD(P)H-dependent enzymes to allow design of new catalytic specificities of these enzymes (e.g. see Scheme 2):
- the assay can be used to screen for active mutants of all the enzymes consuming and generating NADPH and NADH (in the former case the procedure is as in scheme 2, in the latter case the NaOH step should preferably precede the HCl addition—see scheme 2);
- the assay can be adapted to be used with all cells able to express the library of random mutant enzymes of choice;
- the assay can be used to screen for variants of P450 BM3 in their ability to oxidise molecules of environmental interest;
- the assay can be used to screen for variants of P450 BM3 in their ability to catalyse stereo-specific oxidative reactions on fine chemicals.

Data in support of the present invention were obtained with P450 BM3 expressed in *E.coli* BL21(DE3).

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

References

1. Wong, L. L. Cytochrome P450 monooxygenases. *Curr. Opin. Chem. Biol.* 2, 263–268 (1998).
2. Matson, R. S., Hare, R. S., & Fulco, A. J. Characterisation of a cytochrome P-450-dependent fatty acid −2 hydroxylase from *Bacillus megaterium*. *Biochim. Biophys. Acta* 487, 487–494 (1977).
3. Boddupali, S. S., Estabrook, R. W. & Peterson, J. A. Fatty acid monooxygenation by cytochrome P450 BM3. *J. Biol. Chem.* 265, 4233–4239 (1990).
4. Fulco, A. J. P450 BM3 and other inducible bacterial P450 cytochromes: biochemistry and regulation. *Annu. Rev. Pharmacol. Toxicol.* 31, 117–203 (1991).
5. Govindaraj, S., & Poulos, T. L. The domain architecture of cytochrome P450 BM3. *J. Biol. Chem.* 272, 7915–7922 (1997).
6. Narhi, L. O. & Fulco, A. J. Characterisation of a catalytically self-sufficient 119,000-Dalton cytochrome P-450 monooxygenase induced by barbiturates in *Bacillus megaterium*. *J. Biol. Chem.* 261, 7160–7169 (1986).
7. Alworth, W. L., Xia, Q. W. & Liu, H. M. Organochlorine substrates and inhibitors of P450 BM3. *FASEB J.* .11, No 9.ss, P190 (1997).
8. Shaw, A. N. J., Oliver, C. F., Modi, S., Primrose, W. U. Lian, L. Y. & Roberts, G. C. K. The hydroxylation of 11-phenoxyundecanoic acid by wild-type and mutant cytochrome P450 BM3. *FASEB J.* .11, No 9.ss, P218 (1997).
9. Coon M. J. et al. Novel substrates for mechanistic studies with cytochrome P450 BM3. *FASEB J.* 11, No 9.ss, P221 (1997).
10. Wong, L-L, Westlake, A. C. G., & Nickerson, D. P. Protein engineering of cytochrome P450$_{cam}$. *Structure and Bonding* 88, 175–208 (1997).
11. Loida, P. J., & Sligar, S. G. Molecular recognition in cytochrome P-450-cam mechanism for the control of uncoupling reactions. *Biochemistry* 32, 11530–11538 (1993).
12. Yeom, H., Sligar, S. G., Li, H. Y., Poulos, T. L., & Fulco, A. J. The role of Thr268 in oxygen activation of cytochrome P450(BM-3). *Biochemistry* 34, 14733–14740 (1995)
13. Graham-Lowrence, S. et al. An active site substitution, F87V, converts cytochrome P450 BM-3 into a regio- and stereoselective (14S, 15R) arachidonic acid epoxygenase. *J. Biol. Chem.* 272, 1127–1135 (1997).
14. Oliver, C. F., Modi, S., Primrose, W. Lian, L.-Y. & Roberts, G. C. K. Engineering the substrate specificity of *Bacillus megaterium* cytochrome P-450 BM3; hydroxylation of alkyl trimethylammonium compounds. *Biochem. J.* 327, 537–544 (1997).
15. Oliver, C. F. et al. A single mutation in cytochrome P450 BM3 changes substrate orientation in a catalytic intermediate and the regiospecificity of hydroxylation. *Biochemistry* 36, 1567–1572 (1997).
16. Noble, M. A. et al. Roles of key active-site residues in flavocytochrome P450 BM3. *Biochem. J.* 339, 371–379 (1999).
17. Arnold, F. H. Engineering proteins for nonnatural environments. *FASEB J.* 7, 744–749 (1993).

18. Arnold, F. H. & Volkov, A. A. Directed evolution of biocatalysts. *Curr. Opin. Chem. Biol.* 3, 54–59 (1999).
19. Patten, P. A., Howard, R. J. & Stemmer W. P. C. Applications of DNA shuffling to pharmaceuticals and vaccines. *Curr. Opin. Biotechol.* 8, 724–733 (1997).
20. Maves, S. A., Yeom, H., McLean, M. A. & Sligar, S. G. Decreased substrate affinity upon alteration of the substrate-docking region in cytochrome P450 BM3. *FEBS Lett.* 414, 213–218 (1997).
21. Schwaneberg, U., SchmidtDannert, C. A, Schmitt, J. & Schmid, R. D. A continuous spectrophotometric assay for P450 BM-3, a fatty acid hydroxylating to enzyme, and its mutant F87A. *Anal. Biochem.* 269, 359–366 (1999).
22. Joo, H., Lin, Z. & Arnold, F. H. Laboratory evolution of peroxide-mediated cytochrome P450 hydroxylation. *Nature* 399, 670–673 (1999).
23. Parikh, A., Josephy, D. & Guengerich, P. Selection and characterisation of human cytochrome P450 1A2 mutants with altered catalytic properties. *Biochemistry.* 38, 5283–5289 (1999).
24. Grigoryev, D. N. et al. Cytochrome P450c17-expressing *Escherichia coli* as a first-step screening system for 17α-hydroxylase-$C_{17,20}$-lyase inhibitors. *Anal. Biochem.* 267, 319–330 (1999).
25. Kaplan, N. O., Colowick, S. P., & Barnes, C. C. Effect of alkali on diphosphopyridine nucleotide. *J. Biol. Chem.* 191, 461–472 (1951).
26. Lowry, O. H., Roberts, N. R. & Kapphahn, J. I. The fluorometric measurement of pyridine nucleotides. *J. Biol. Chem.* 224, 1047–1064 (1957).
27. Ruettinger, R. T., Wen, L. P., & Fulco, A. J. Coding nucleotide, 5' regulatory, and deduced amino acid sequences of P450 BM3, a single peptide cytochrome P-450:NADPH-P-450 reductase from *Bacillus megaterium*. *J. Biol. Chem.* 264, 10987–10995 (1989).
28.
29.
30.
31. Childs, R. E. & Bardsley, W. G. The steady-state kinetics of Peroxidase with 2'2-Azino-di(3-ethyl-benzathiazoline-6-sulphonic acid) as chromogen. *Biochem. J.* 145, 93–103 (1975).
32. Narhi, L. O. & Fulco, A. J. Characterisation of a catalytically self-sufficient 119,000-Dalton cytochrome P-450 monooxygenase induced by barbiturates in *Bacillus megaterium*. *J. Biol. Chem.* 261, 7160–7169 (1986).
33. Darwish, K., Li, H., & Poulos T. L. Engineering proteins, subcloning and hyperexpressing oxidoreductase genes. *Protein Eng.* 4, 701–708 (1991).
34. Li, H., Darwish, K., & Poulos T. L. Characterisation of recombinant *Bacillus megaterium* cytochrome P450 BM3 and its two functional domains. *J. Biol. Chem.* 266, 11909–11914 (1991).

What is claimed is:

1. A process for detecting modulation of NAD(P)H and/or a NAD(P)H dependent oxidoreductase ("NDO") in or by a biological system which comprises NAD(P)H and an NDO; said process comprising generating a detectable marker of: NAD(P)H modulation and/or NDO modulation, and detecting said detectable marker, wherein said detectable marker is generated by alkaline treatment of $NAD(P)^+$ or an analogue thereof.

2. A process according to claim 1 wherein said biological system comprises whole cell(s).

3. A process according to claim 1 or claim 2 wherein said biological system also comprises a substrate for said NDO.

4. A process according to claim 3 wherein said substrate is a putative biologically useful agent.

5. A process according to claims 1 or 2 wherein said NAD(P)H modulation is NAD(P)H consumption.

6. A process according to claims 1 or 2 wherein said process further comprises the step of quantifying said modulation.

7. A process according to claims 1 or 2 wherein said detection is via spectrometric techniques.

8. A biological system for use in a process for detecting modulation of NAD(P)H and/or a NAD(P)H dependent oxidoreductase ("NDO"), wherein said biological system comprises NAD(P)H and an NDO; wherein said biological system is capable of generating a detectable marker of NAD(P)H modulation and/or NDO modulation, wherein said detectable marker is capable of being generated by alkaline treatment of $NAD(P)^+$ or an analogue thereof.

9. A biological system according to claim 8 wherein said biological system is a whole cell.

10. A biological system according to claim 8 or claim 9 wherein said cell is an *E. coli* cell.

11. A biological system for use in a process for detecting modulation of NAD(P)H and/or a NAD(P)H dependent oxidoreductase ("NDO"), wherein said biological system comprises NAD(P)H and an NDO; wherein said biological system is capable of generating a detectable marker of NAD(P)H modulation and/or NDO modulation; wherein said detectable marker is capable of being generated by alkaline treatment of $NAD(P)^+$ or an analogue thereof; and wherein said biological system is an *E. coli* cell; and wherein said NDO is cytochrome P450 BM3 from *Bacillus megaterium*.

* * * * *